(12) United States Patent
Nagai et al.

(10) Patent No.: US 8,147,754 B2
(45) Date of Patent: Apr. 3, 2012

(54) SAMPLE MEASURING APPARATUS AND SAMPLE MEASURING METHOD

(75) Inventors: Takaaki Nagai, Kobe (JP); Hideaki Matsumoto, Takasago (JP); Yuichi Hamada, Kobe (JP)

(73) Assignee: Sysmex Corporation, Hyogo (JP)

( * ) Notice: Subject to any disclaimer, the term of this patent is extended or adjusted under 35 U.S.C. 154(b) by 899 days.

(21) Appl. No.: 11/729,295

(22) Filed: Mar. 28, 2007

(65) Prior Publication Data

US 2007/0231206 A1 Oct. 4, 2007

(30) Foreign Application Priority Data

Mar. 30, 2006 (JP) .................................. 2006-94947

(51) Int. Cl.
*C12Q 1/68* (2006.01)
*G01N 21/00* (2006.01)
*G01N 33/48* (2006.01)

(52) U.S. Cl. ............................ 422/63; 422/50; 422/68.1
(58) Field of Classification Search ...................... 422/63
See application file for complete search history.

(56) References Cited

U.S. PATENT DOCUMENTS

| 5,506,673 | A | * | 4/1996 | Kosaka et al. ................. 356/72 |
| 6,391,263 | B1 | | 5/2002 | Mishima et al. |
| 2005/0255001 | A1 | * | 11/2005 | Padmanabhan et al. ........ 422/73 |

FOREIGN PATENT DOCUMENTS

| JP | 06-027117 | 2/1994 |
| JP | 06-094729 | 4/1994 |
| JP | 07-128217 | 5/1995 |
| JP | 2000-266757 | 9/2000 |

* cited by examiner

*Primary Examiner* — Jill Warden
*Assistant Examiner* — Dean Kwak
(74) *Attorney, Agent, or Firm* — Brinks Hofer Gilson & Lione

(57) ABSTRACT

A sample measuring apparatus of measuring a component in a biological sample, comprising: an input section for inputting a sample species of a biological sample; a measurement sample preparation section for preparing a measurement sample by mixing the biological sample with a reagent; a first measurement section; a second measurement section being different from the first measurement section; a measurement sample supply section for supplying the measurement sample prepared in the measurement sample preparation section to at least one of the first measurement section and second measurement section; and a control section for controlling the measurement sample supply section based on the inputted sample species.

7 Claims, 25 Drawing Sheets

[Fig. 1]
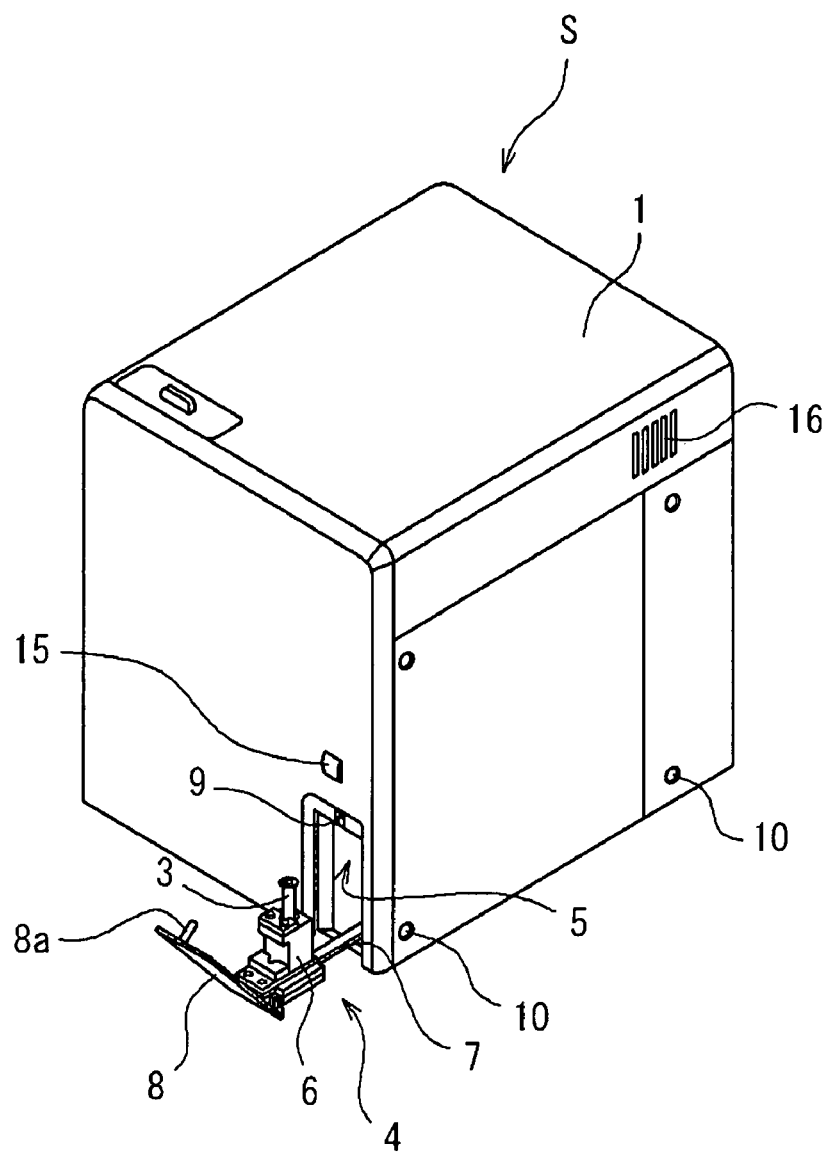

[Fig. 2]
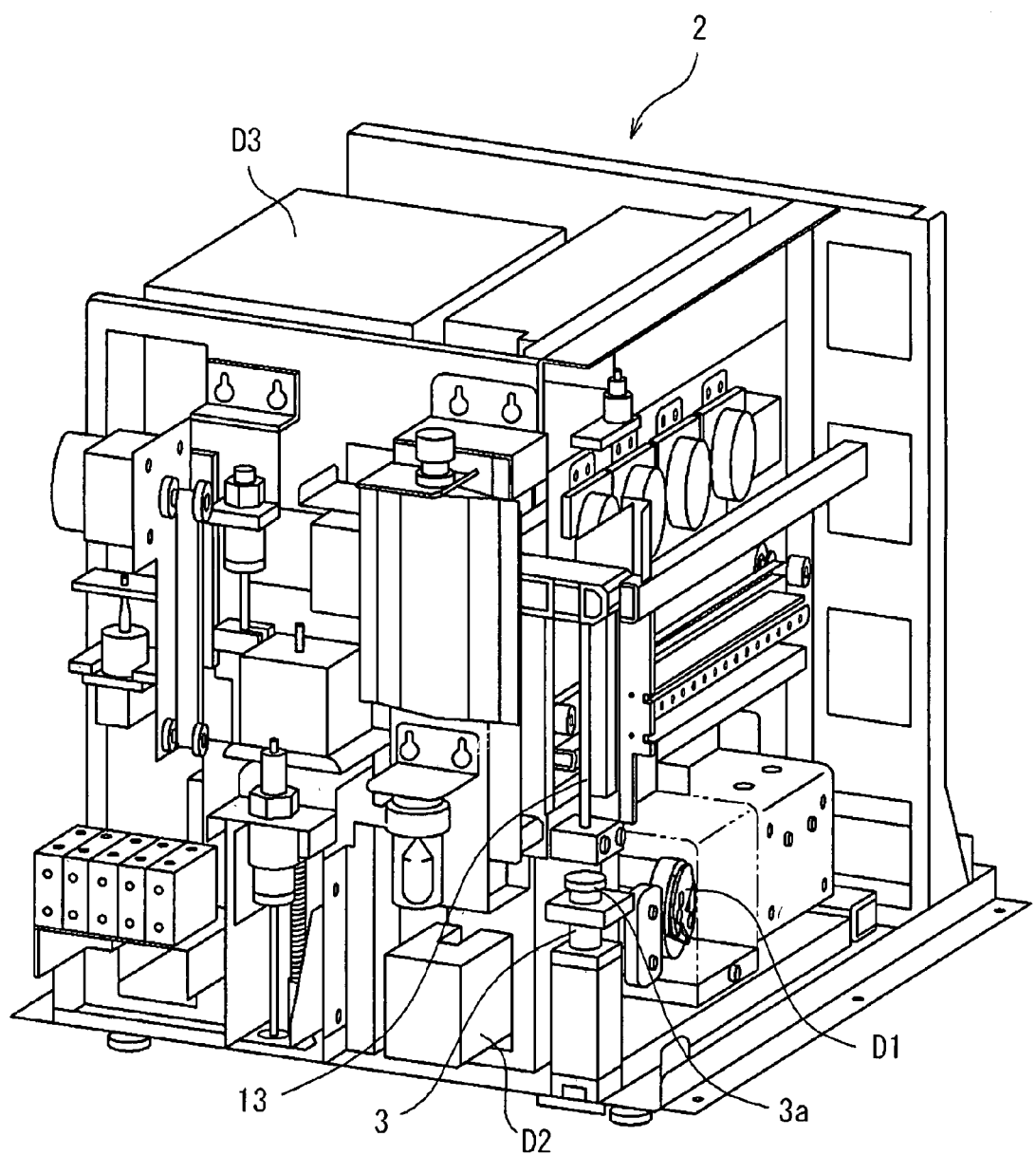

[Fig. 3]
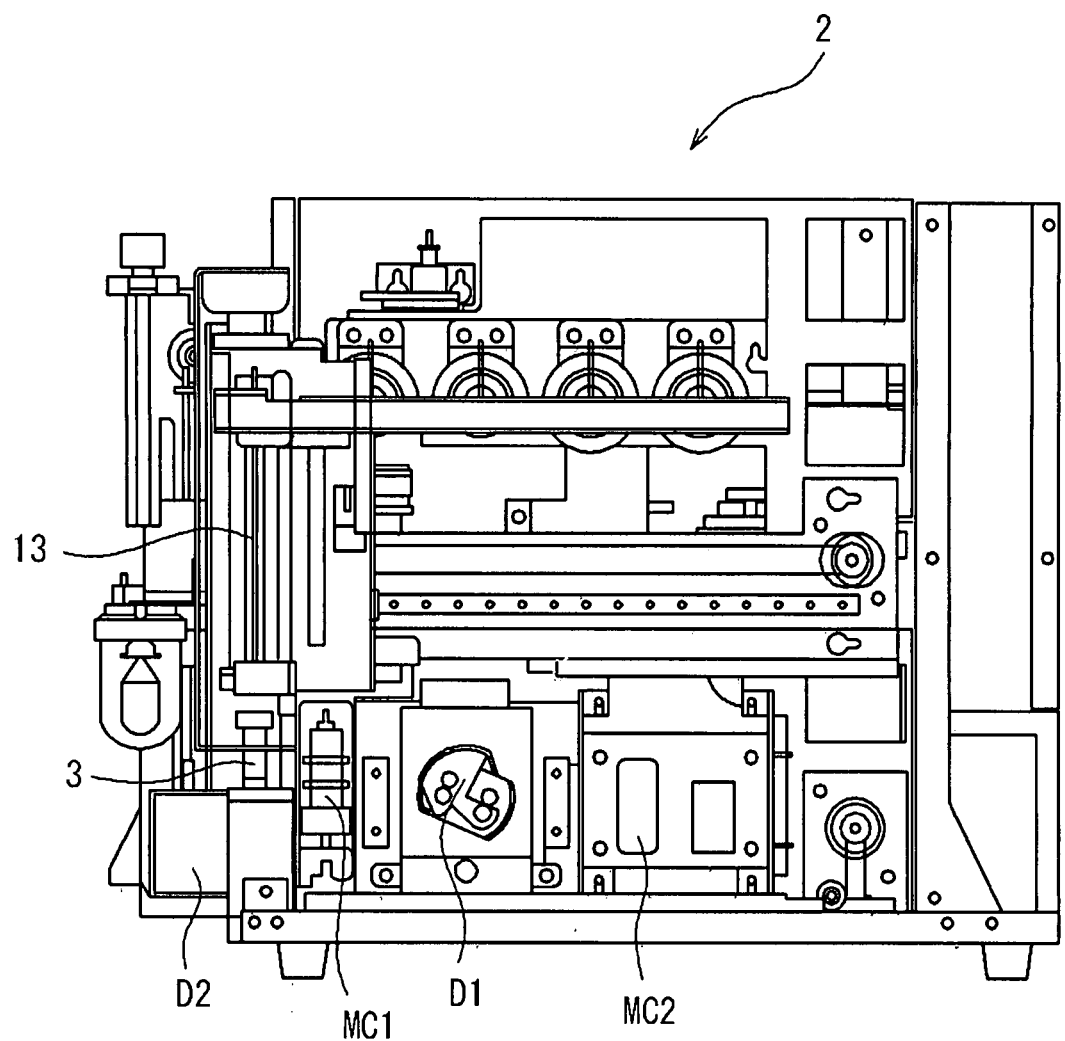

[Fig. 4]
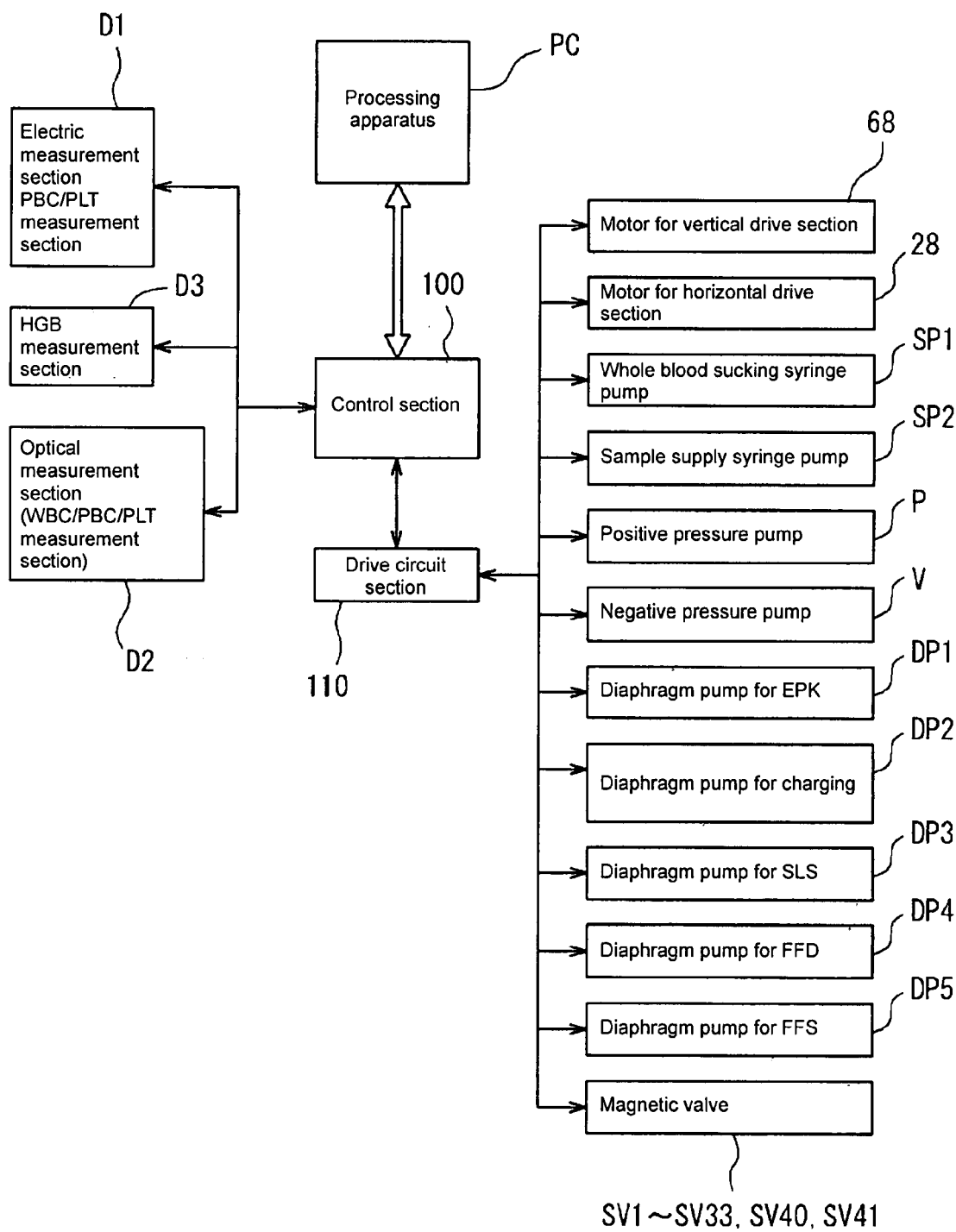

[Fig. 5]
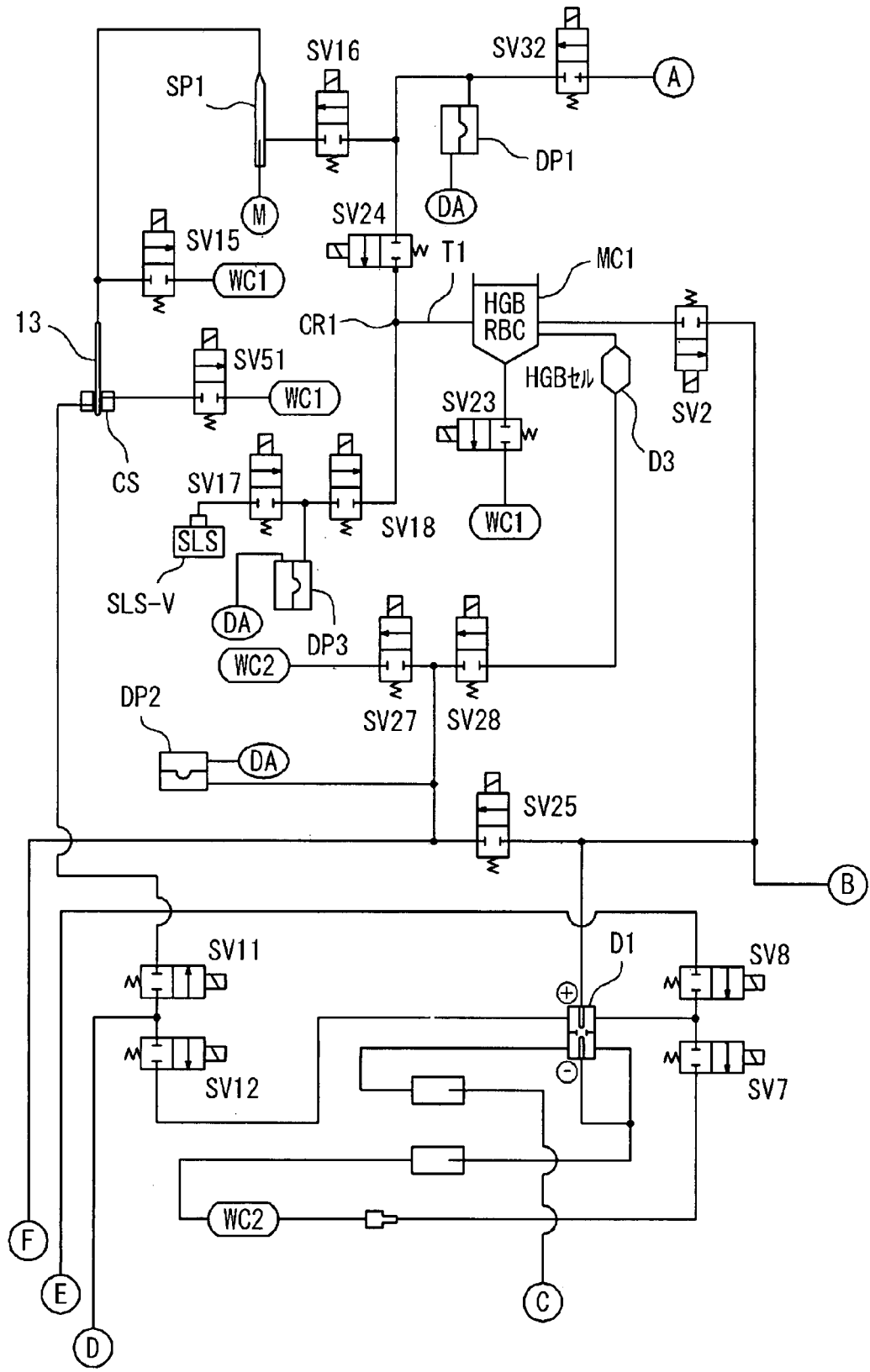

[Fig. 6]
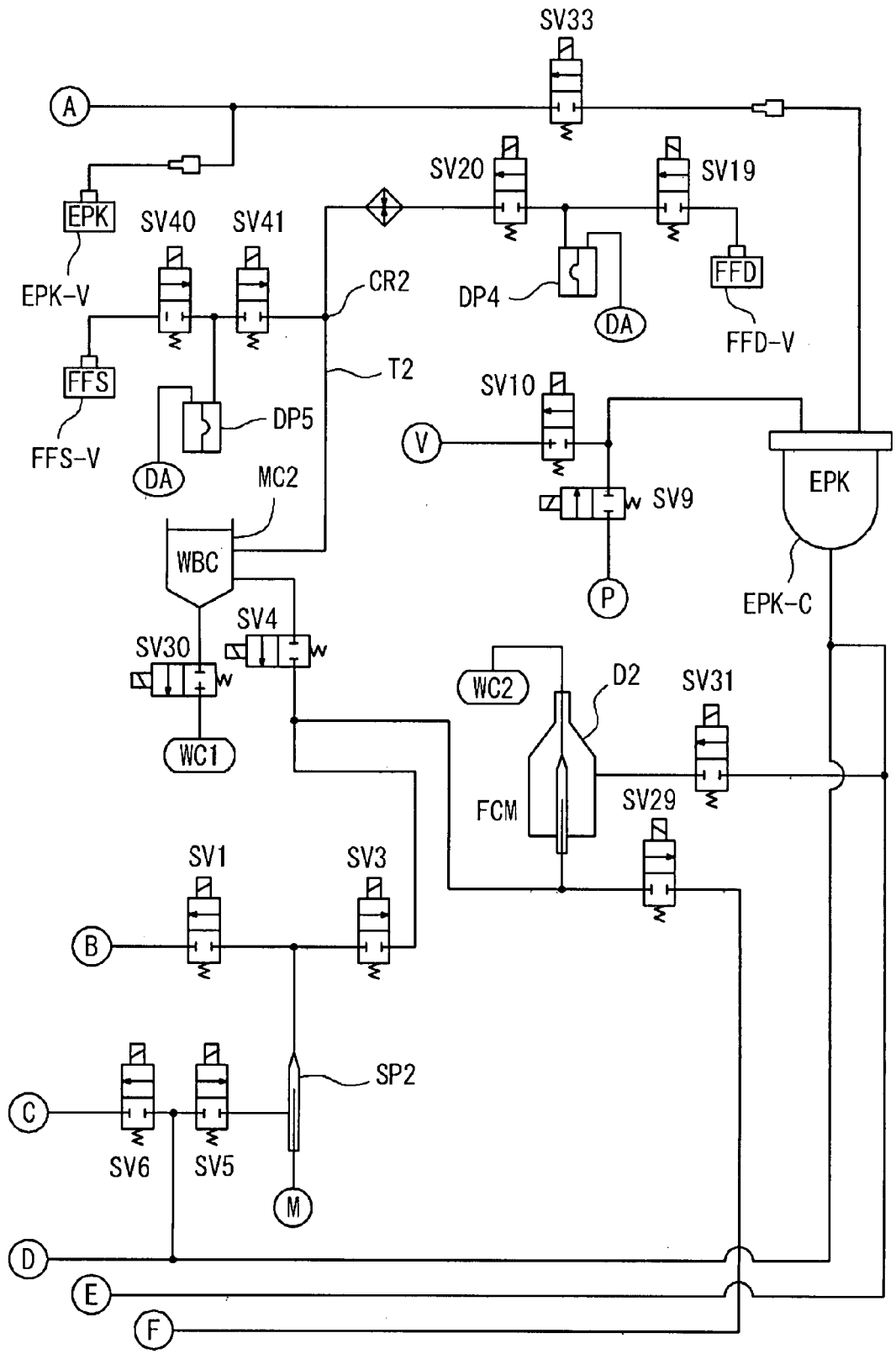

[Fig. 7]
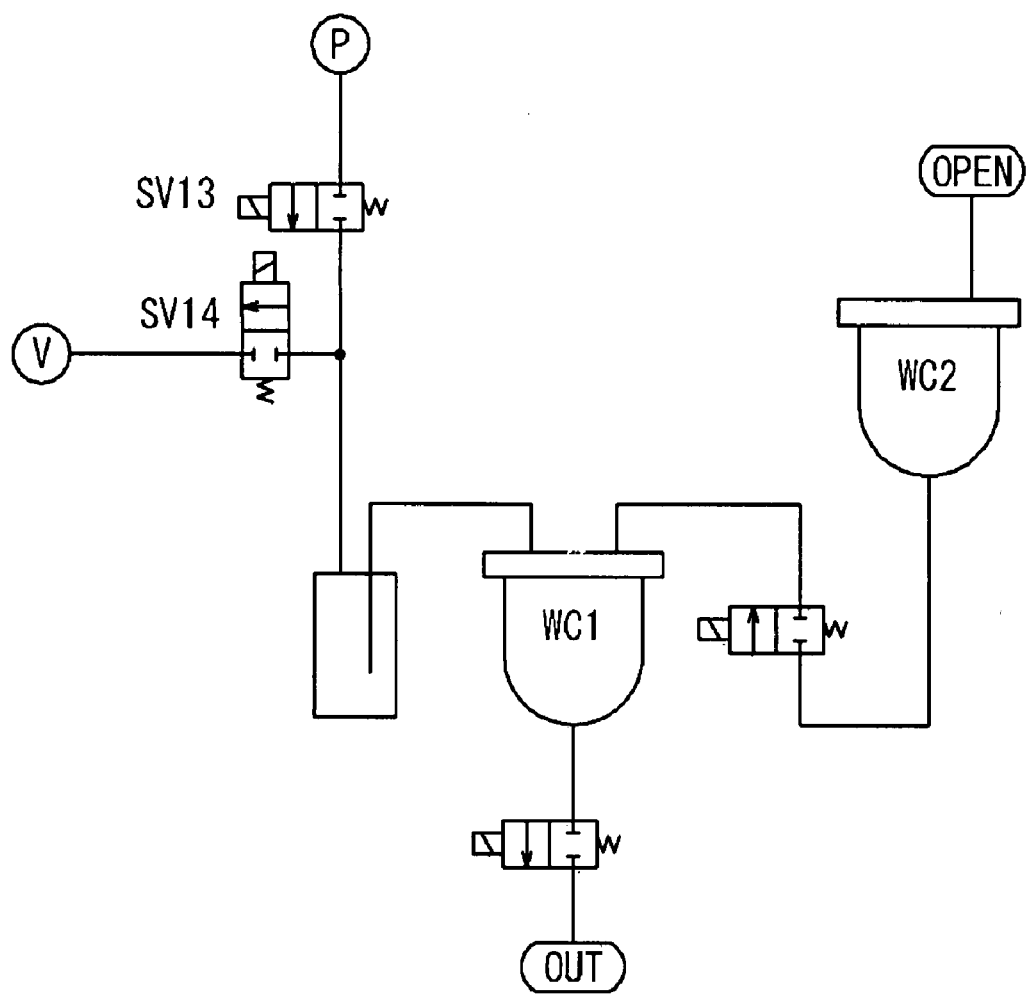

[Fig. 8]
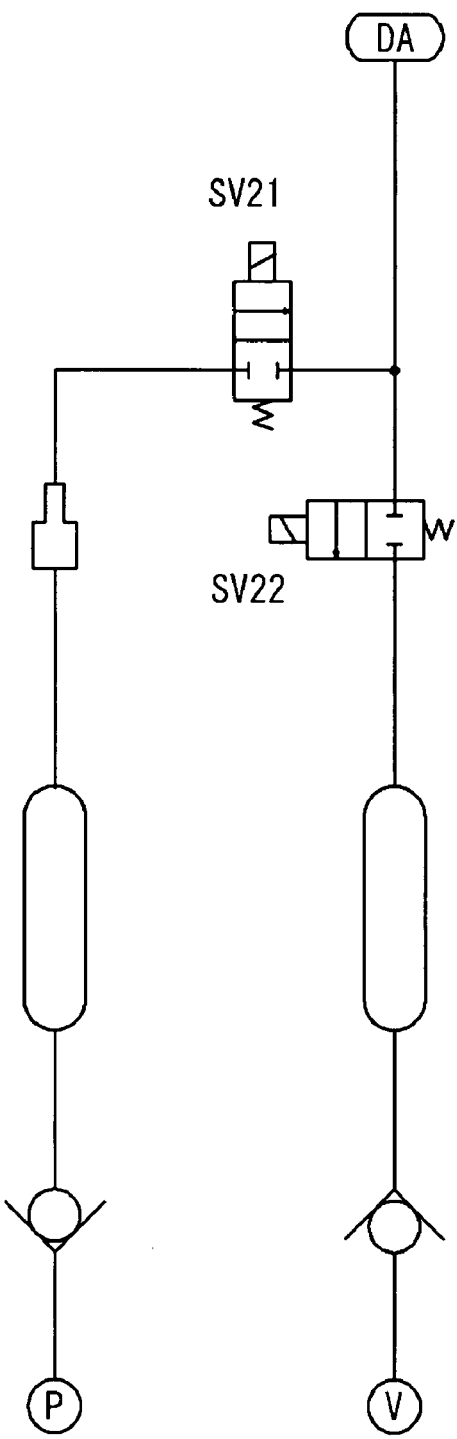

[Fig. 9]
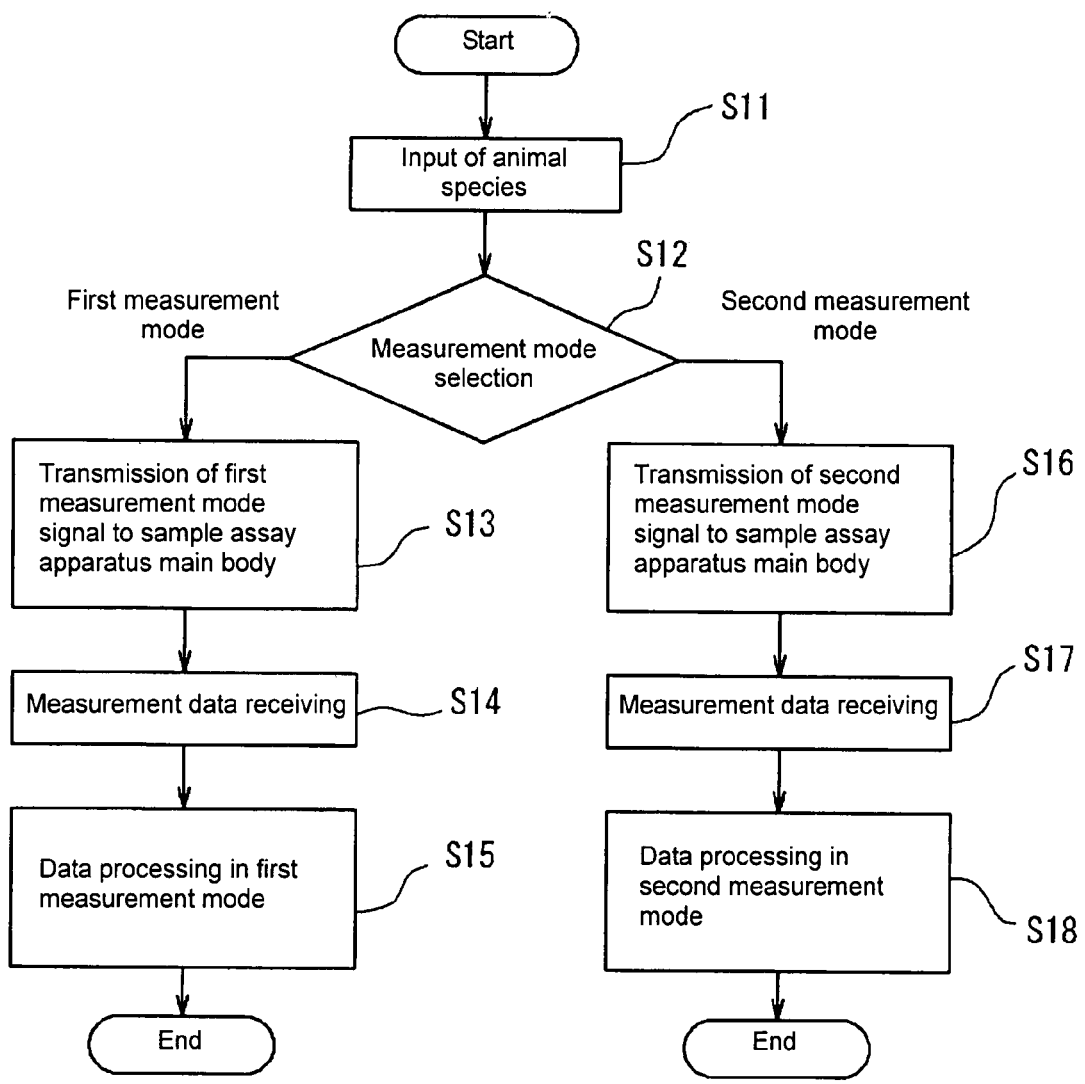

[Fig. 10]

Database of animal species

| Animal species | Measurement mode |
|---|---|
| Dog | 1 |
| Cat | 2 |
| Horse | 1 |
| ⋮ | ⋮ |

[Fig. 11]
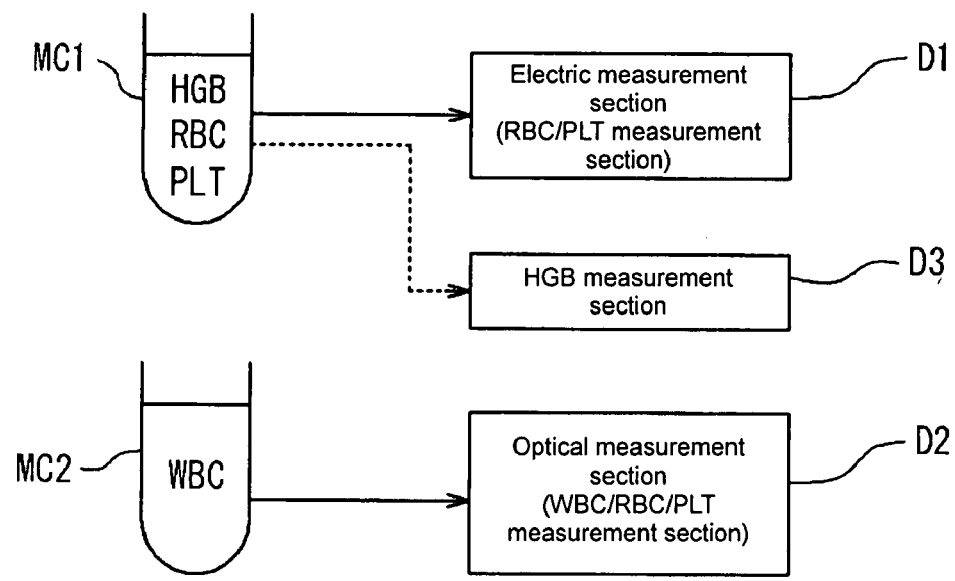

[Fig. 12]
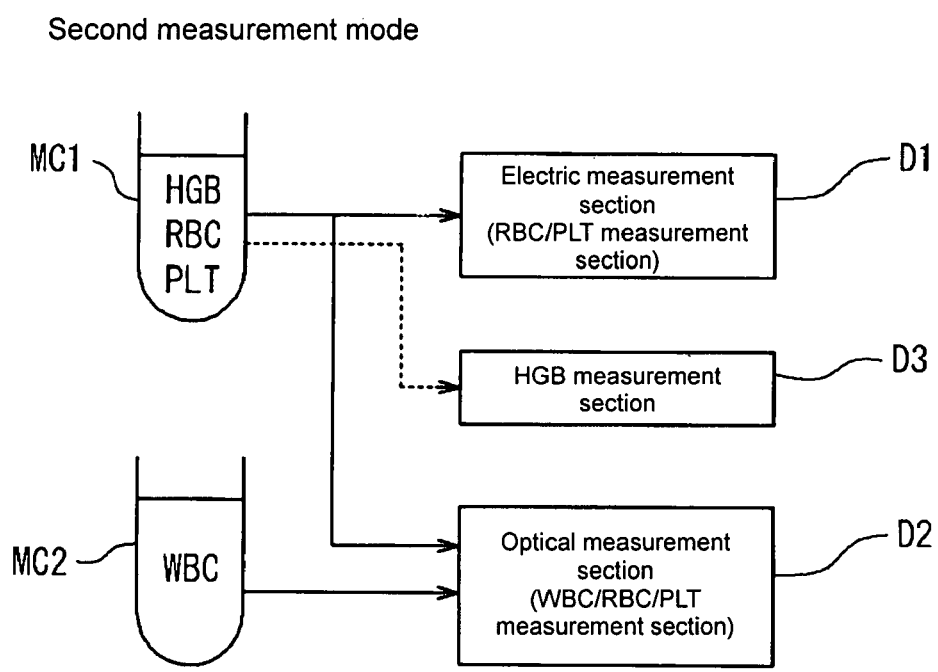

[Fig. 13]
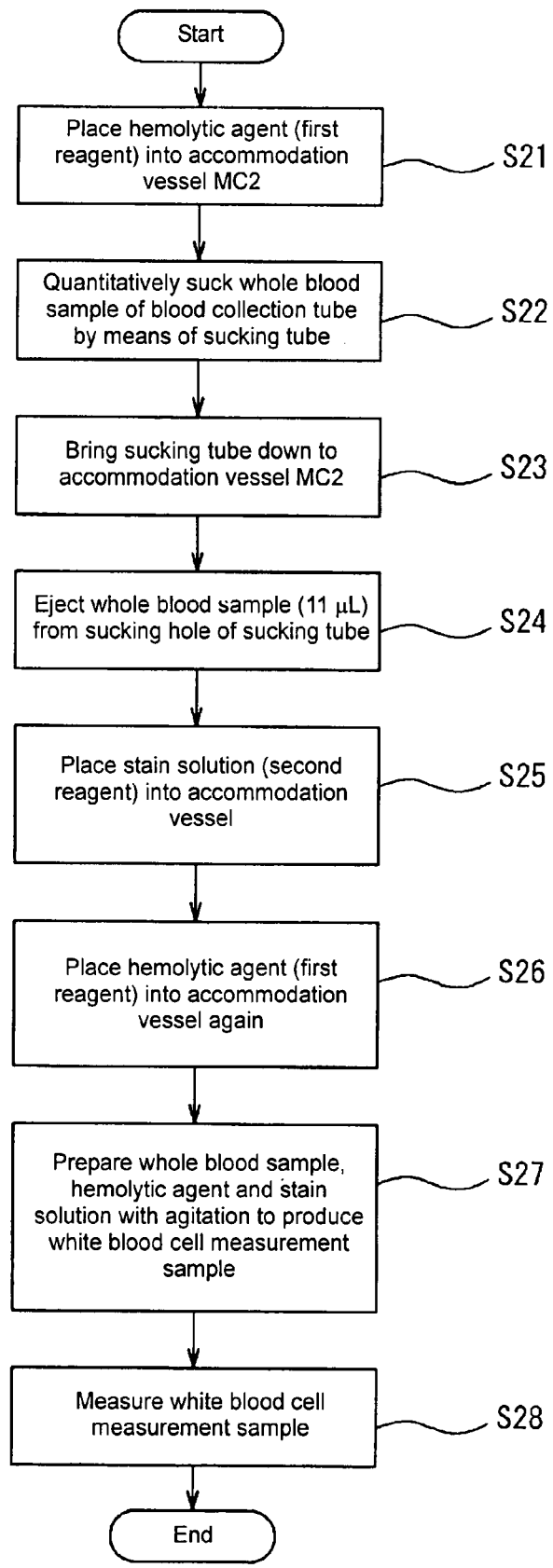

[Fig. 14]
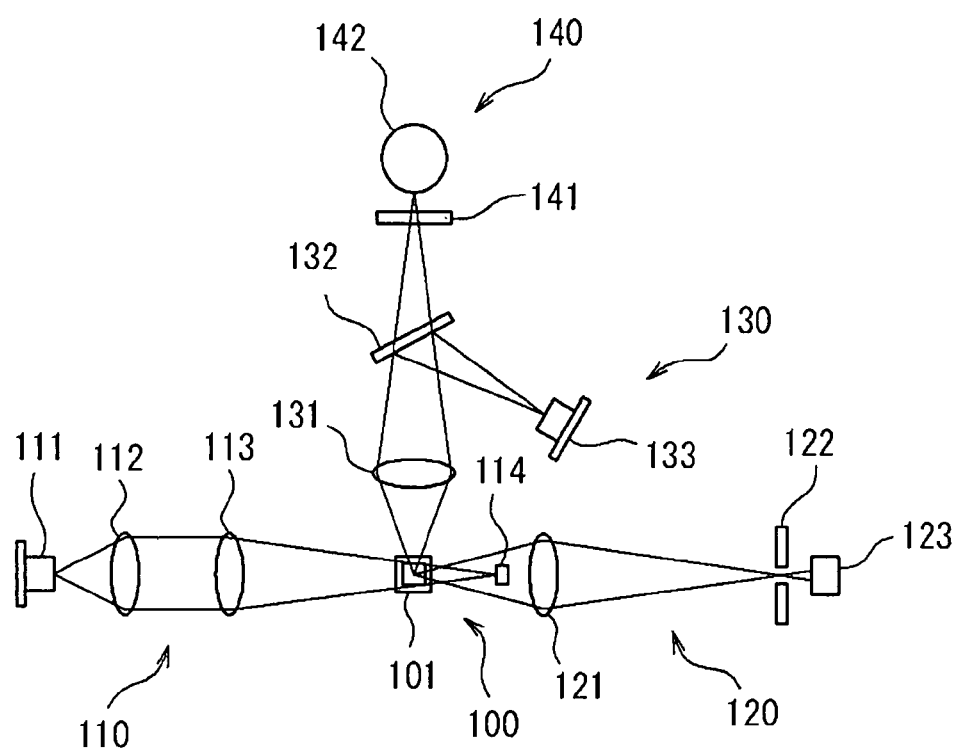

[Fig. 15]
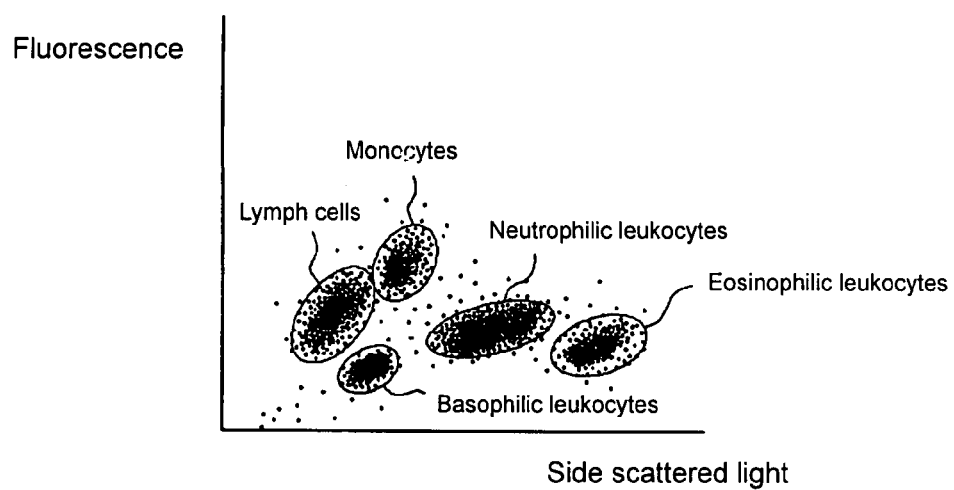

[Fig. 16]
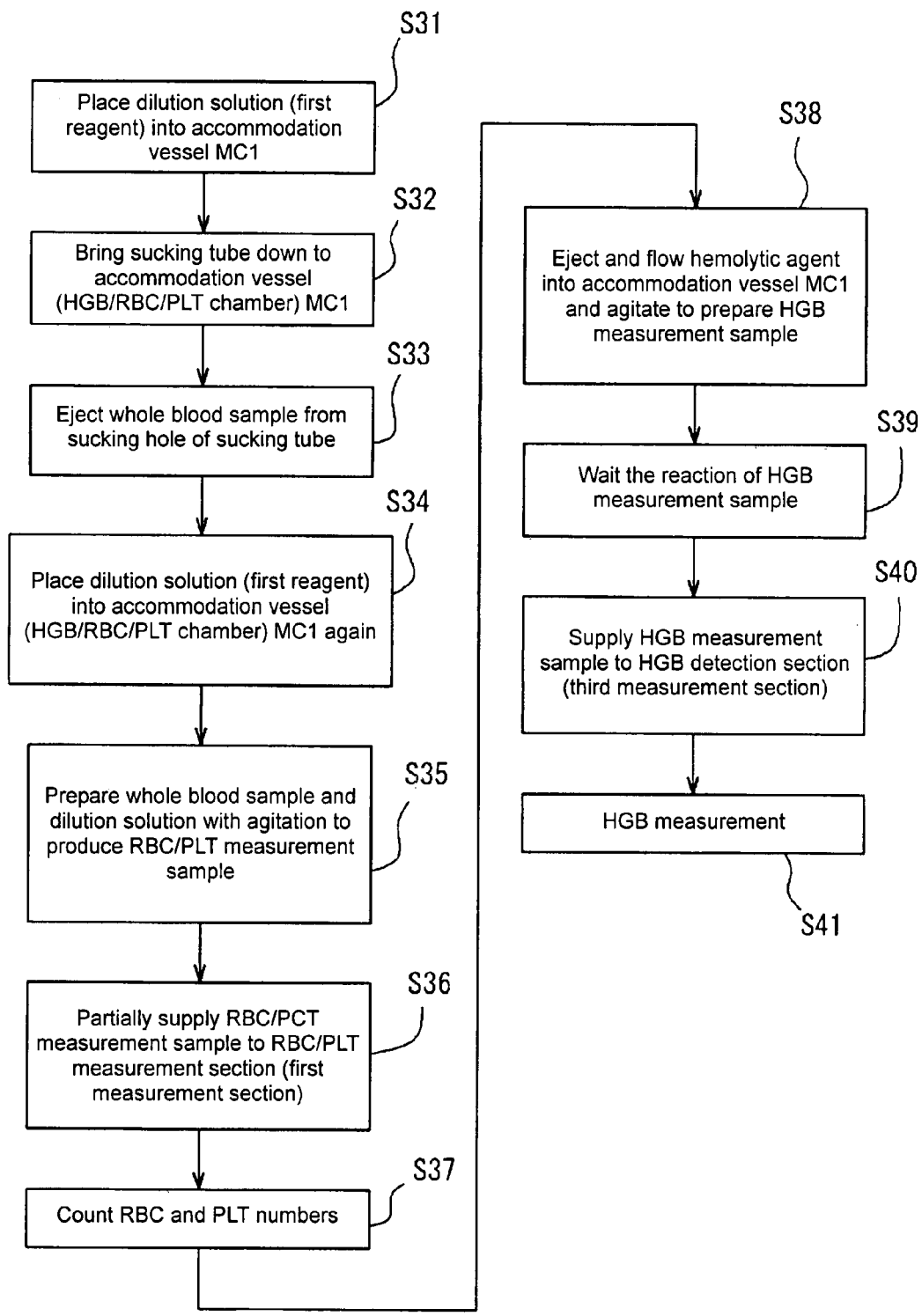

[Fig. 17]
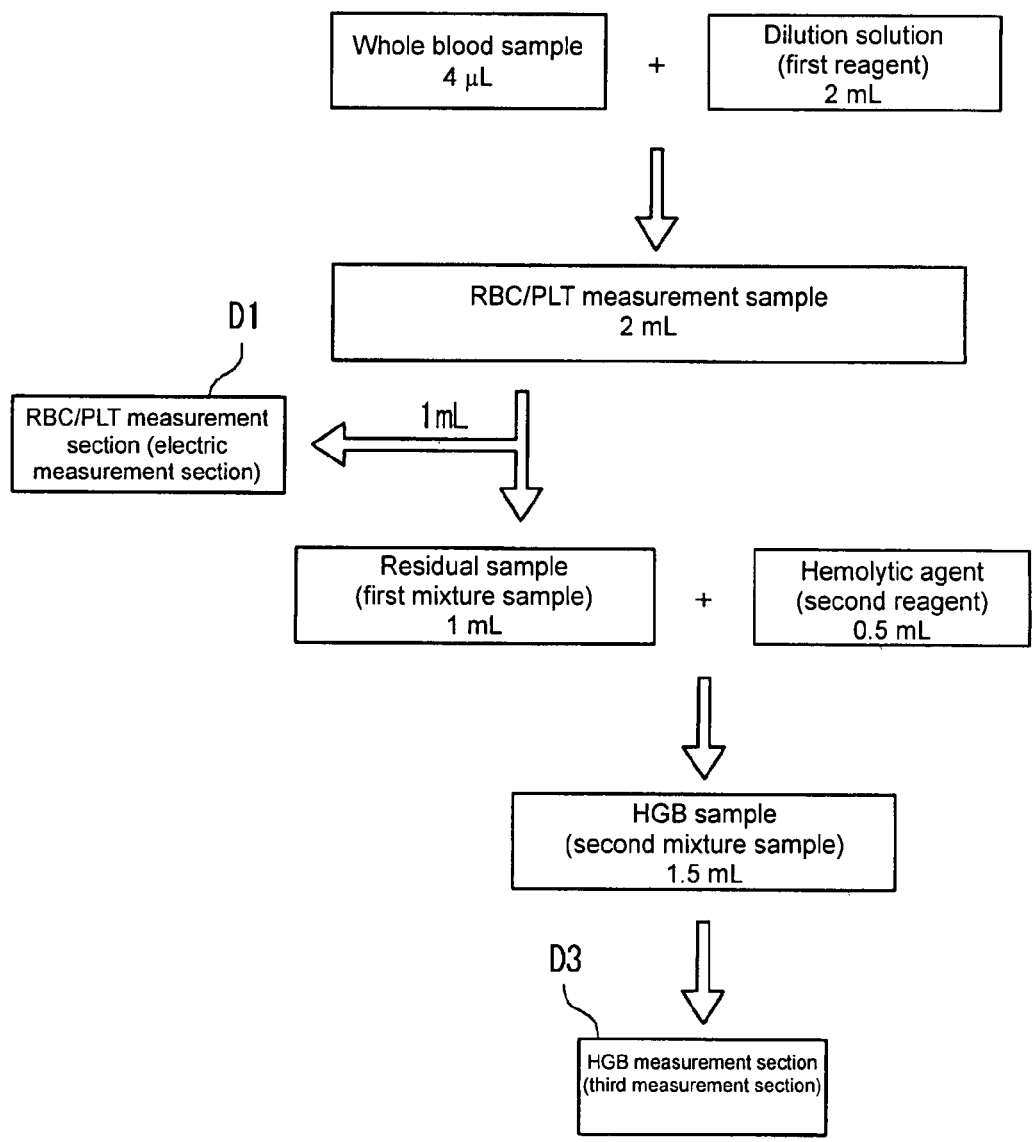

[Fig. 18]
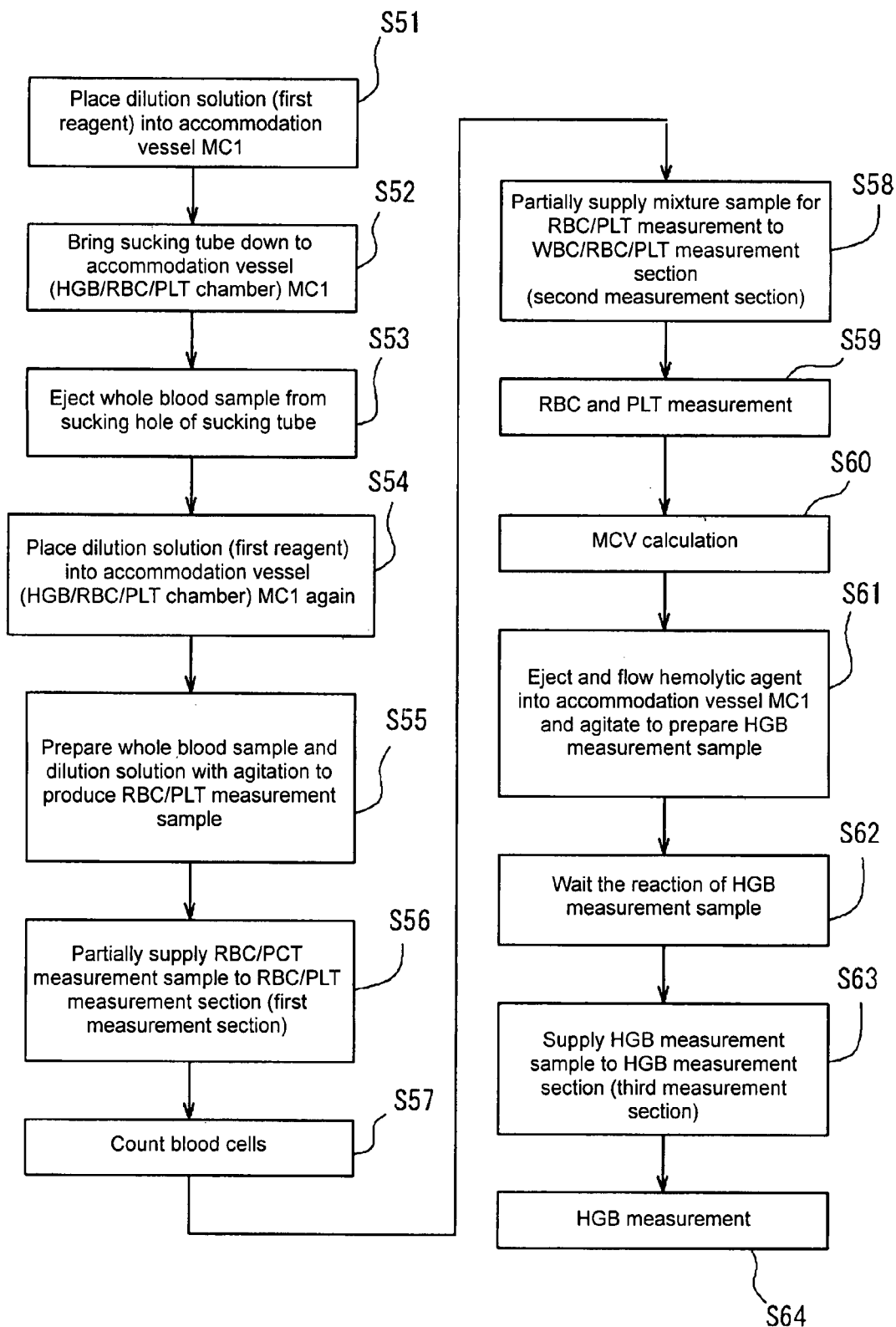

[Fig. 19]
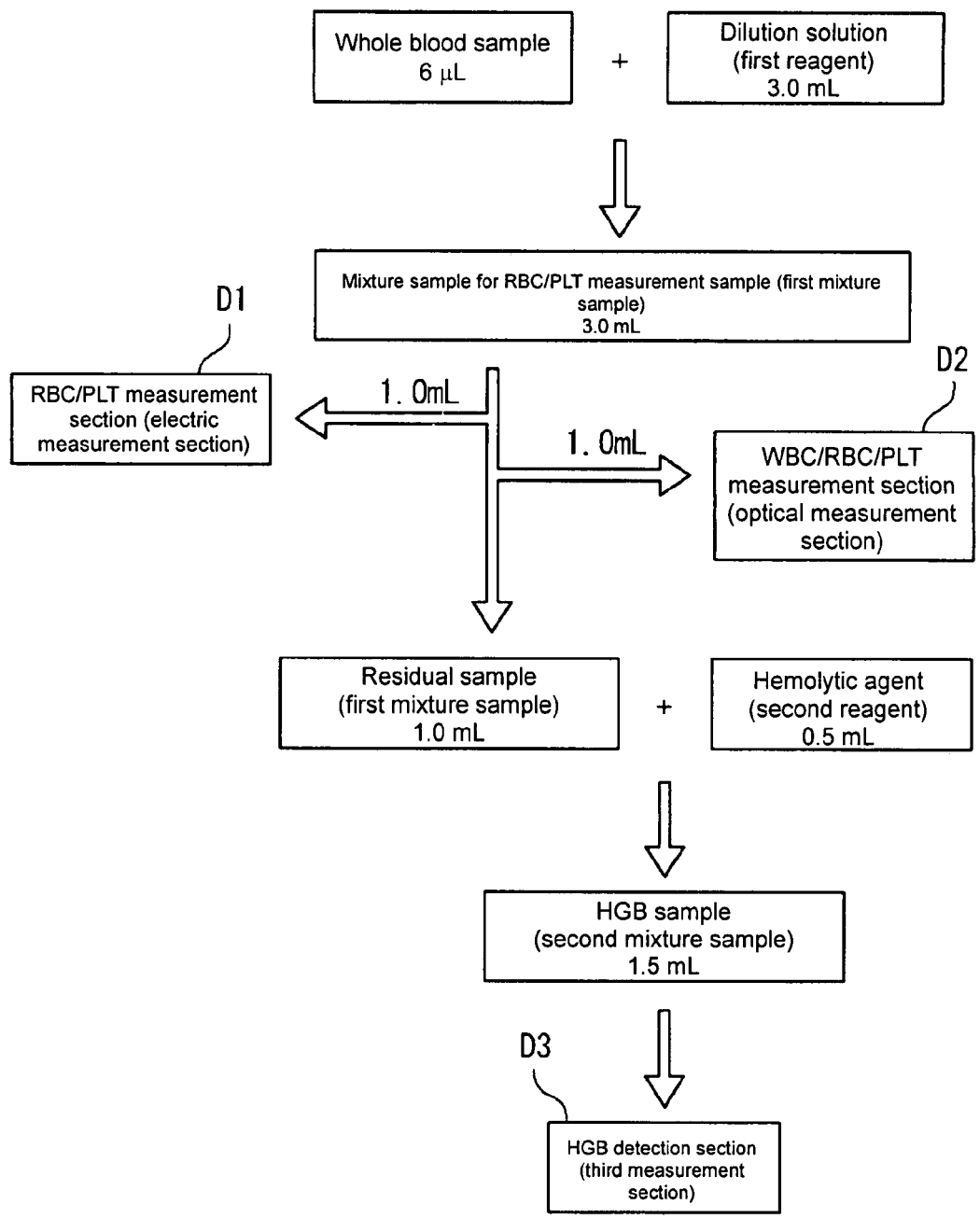

[Fig. 20]
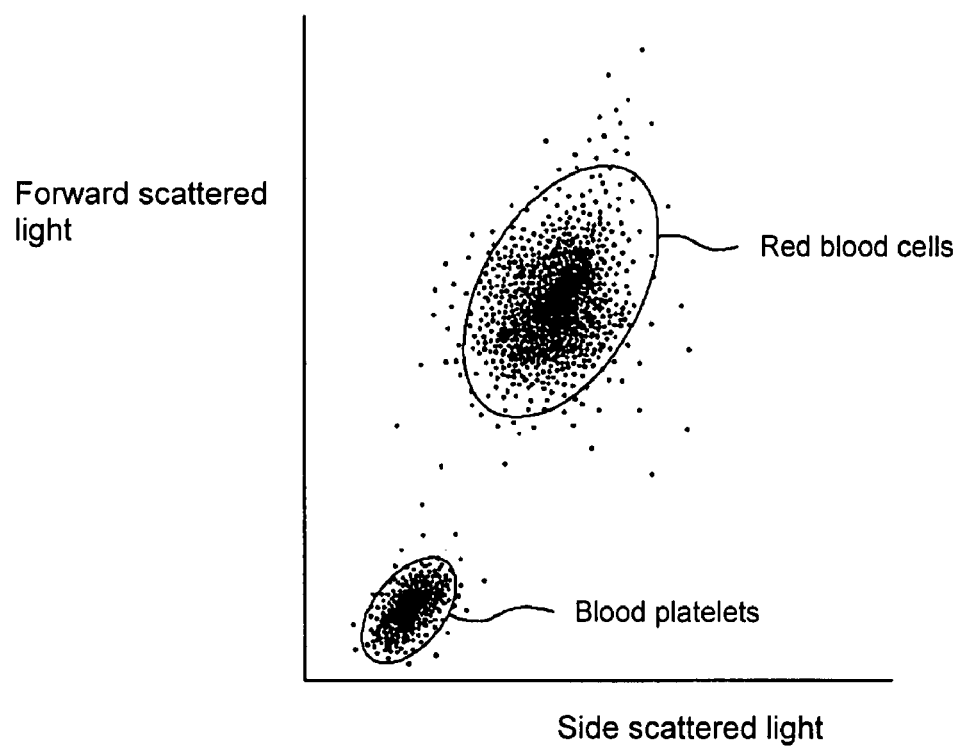

[Fig. 21]
First measurement mode
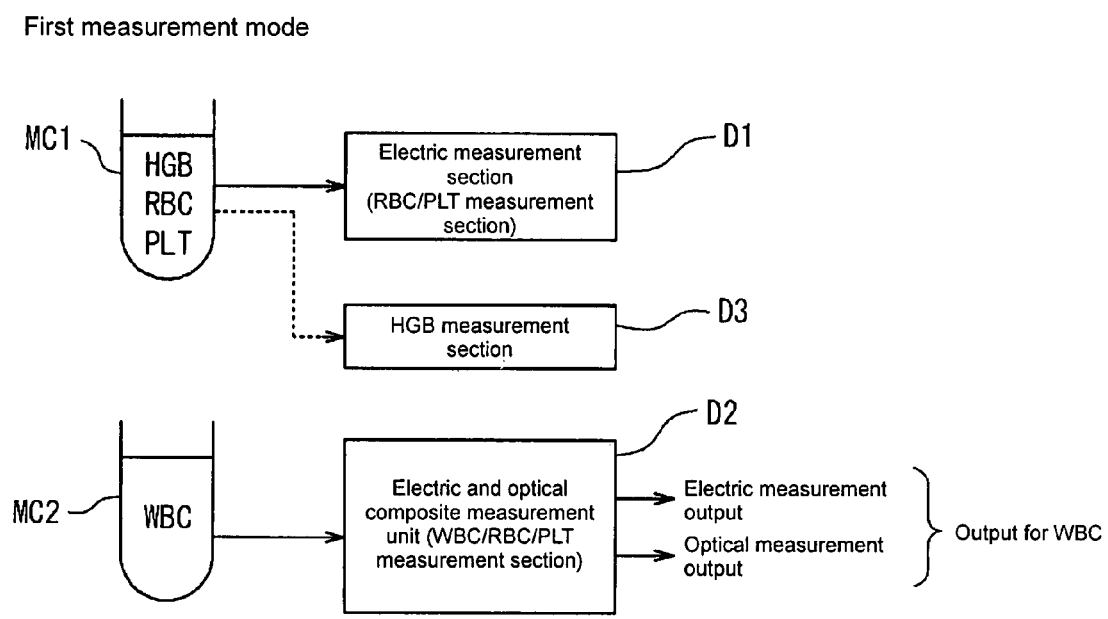

[Fig. 22]
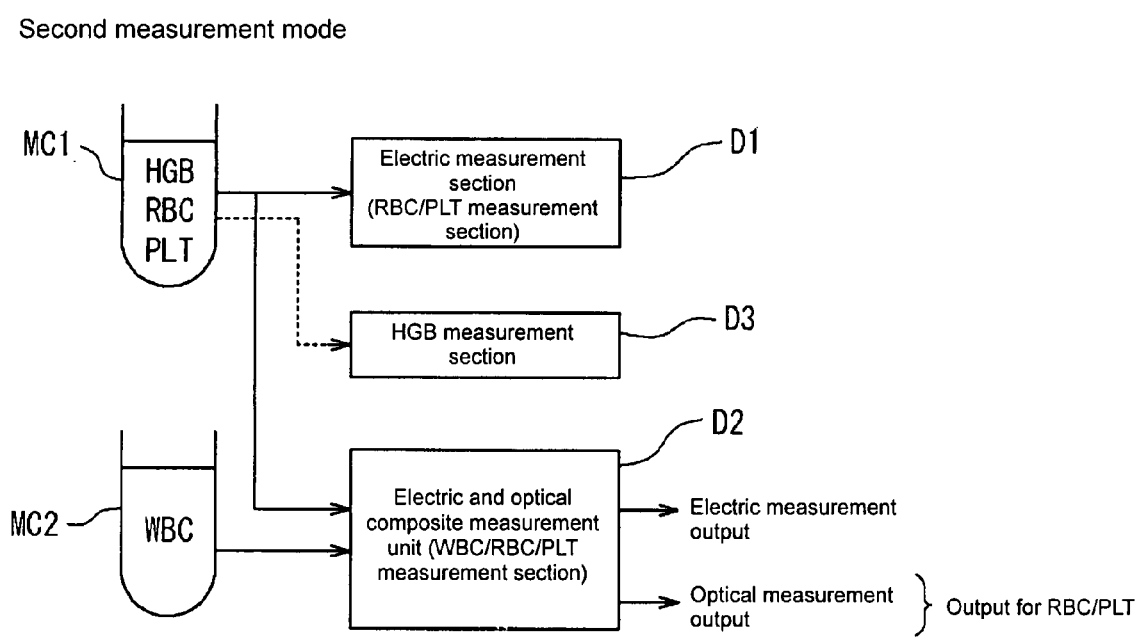

[Fig. 23]
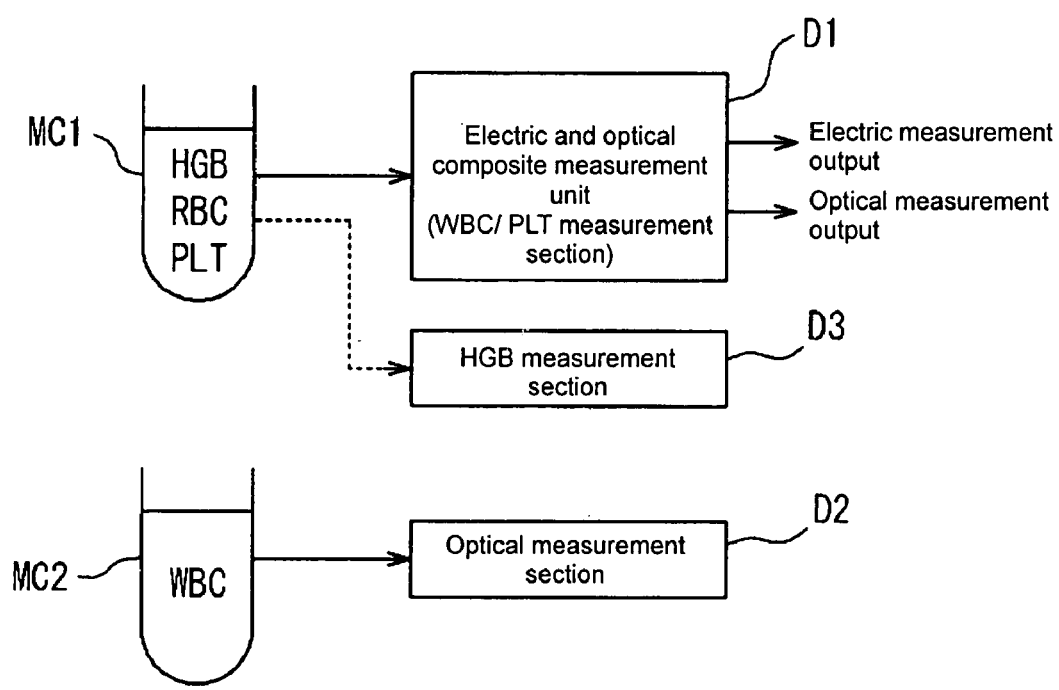

[Fig. 24]
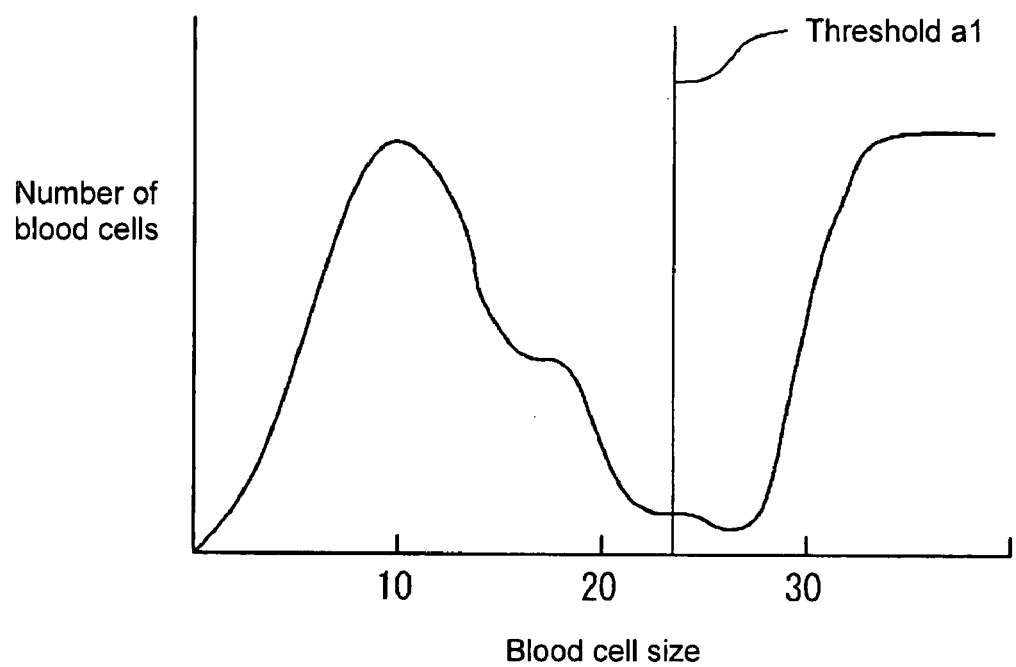

[Fig. 25]
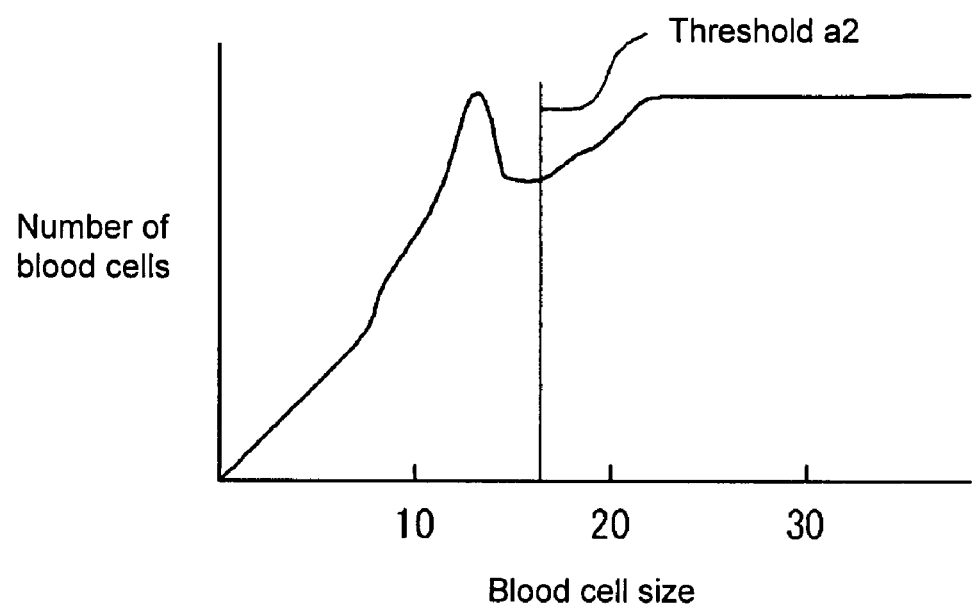

SAMPLE MEASURING APPARATUS AND SAMPLE MEASURING METHOD

RELATED APPLICATIONS

This application claims priority under 35 U.S.C. §119 to Japanese Patent Application No. JP2006-094947 filed Mar. 30, 2006, the entire content of which is hereby incorporated by reference.

FIELD OF THE INVENTION

The present invention relates to a sample measuring apparatus and sample measuring method.

BACKGROUND OF THE INVENTION

Recently, as a pet boom spreads, apparatuses examining animals have been developed so as to be capable of coping with the sophistication of animal medications and various species of animals. In particular, in blood cell assay apparatuses of measuring blood cells in animal bloods, apparatuses capable of classifying blood cells as well as counting the number of blood cells and apparatuses capable of automatically changing measurement sensitivity adapting to the species of animals have been developed and used in many animal hospitals and animal experiment facilities.

As such a blood cell assay apparatus, there exists a sample measuring apparatus of assaying a biological sample of a different species of animals, which is configured so as to alter the measurement sensitivity for adapting for species of animals inputted by means of input means of species of animals (U.S. Pat. No. 6,391,263).

However, only alteration of measurement sensitivity cannot obtain precise measurement results in some cases.

SUMMARY OF THE INVENTION

The scope of the present invention is defined solely by the appended claims, and is not affected to any degree by the statements within this summary.

A first aspect of the present invention is a sample measuring apparatus of measuring a component in a biological sample, comprising: an input section for inputting a sample species of a biological sample; a measurement sample preparation section for preparing a measurement sample by mixing the biological sample with a reagent; a first measurement section; a second measurement section being different from the first measurement section; a measurement sample supply section for supplying the measurement sample prepared in the measurement sample preparation section to at least one of the first measurement section and second measurement section; and a control section for controlling the measurement sample supply section based on the inputted sample species.

A second aspect of the present invention is a sample measuring apparatus of measuring a component in a biological sample, comprising: an input section for inputting a sample species of the biological sample; a measurement sample preparation section of preparing a measurement sample by mixing the biological sample with a reagent; a measurement section for measuring the measurement sample by means of at least one of a first measurement principle and a second measurement principle being different from the first measurement principle; and a control section for controlling the measurement section so as to measure first and second components in the biological sample by the first measurement principle when the sample species of the biological sample is a first sample species, and for controlling the measurement section so as to measure the second component in the biological sample by the first measurement principle and the first component in the biological sample by the second measurement principle when the sample species of the biological sample is a second sample species.

A third aspect of the present invention is a method of measuring a component in a biological sample, comprising steps of: receiving a sample species of the biological sample; and measuring first and second components in the biological sample by a first measurement principle when the sample species of the biological sample is a first sample species, or measuring the second component in the biological sample by the first measurement principle and the first component in the biological sample by a second measurement principle when the sample species of the biological sample is a second sample species.

BRIEF DESCRIPTION OF THE DRAWINGS

FIG. 1 is a perspective view of the whole of a sample measuring apparatus (main body) according to one embodiment of the present invention.

FIG. 2 is a perspective view of the sample measuring apparatus (main body) illustrated in FIG. 1 with the casing being removed.

FIG. 3 is a front depiction view of the sample measuring apparatus (main body) illustrated in FIG. 1 with the casing being removed.

FIG. 4 is a block diagram of the control of the sample measuring apparatus.

FIG. 5 shows the first half portion of a fluid circuit diagram of the sample measuring apparatus illustrated in FIG. 1.

FIG. 6 shows the latter half portion of a fluid circuit diagram of the sample measuring apparatus illustrated in FIG. 1.

FIG. 7 is a fluid circuit diagram surrounding a drainage chamber.

FIG. 8 is a fluid circuit diagram surrounding a diaphragm pump.

FIG. 9 shows a flow chart related to measurement mode selection.

FIG. 10 is a diagram indicating a database of species of animals.

FIG. 11 is a block diagram indicating the measuring section used in a first measurement mode.

FIG. 12 is a block diagram indicating the measuring section used in a second measurement mode.

FIG. 13 shows a flow chart of white blood cell measurement.

FIG. 14 is a schematic block diagram of an optical measurement section.

FIG. 15 is a scattergram indicating five classifications of white blood cells.

FIG. 16 is a flow chart indicating a measurement procedure of RBC/PLT measurements and HGB measurement in the first measurement mode.

FIG. 17 is a schematic view of the preparation step of a measurement sample in the first measurement mode.

FIG. 18 is a flow chart indicating a measurement procedure of RBC/PLT measurements and HGB measurement in the second measurement mode.

FIG. 19 is a schematic view of the preparation step of a measurement sample in the second measurement mode.

FIG. 20 is a scattergram produced by discriminating red blood cells and blood platelets by means of side scattered light and forward scattering light.

FIG. 21 is a block diagram (first measurement mode) indicating the measurement section according to Modified Example 1.

FIG. 22 is a block diagram (second measurement mode) indicating the measurement section according to Modified Example 1.

FIG. 23 is a block diagram indicating the measurement section according to Modified Example 2.

FIG. 24 is a histogram indicating the number of blood cells when blood of a dog was measured via an electric measurement section.

FIG. 25 is a histogram indicating the number of blood cells when blood of a cat was measured via an electric measurement section.

DETAILED DESCRIPTION OF THE PREFERRED EMBODIMENTS

Embodiments of the present invention will be set forth in detail with reference to appended drawings hereinafter.

A sample measuring apparatus according to embodiments includes a sample measuring apparatus main body S and a processing apparatus PC.

[Whole Construction of Sample Measuring Apparatus Main Body]

FIG. 1 is a perspective view of the whole of the sample measuring apparatus main body S; FIG. 2 is a perspective view of this sample measuring apparatus main body S with a casing 1 being removed; and FIG. 3 is a front depiction view with the casing being removed in the same manner.

This sample measuring apparatus main body S is connected in a communication-possible fashion to the processing apparatus PC (typically, a personal computer in which a required computer program is installed) having a display, input device, CPU, memory and other devices (see FIG. 4).

The processing apparatus PC has installed therein software for the sample measuring apparatus, which carries out the operation of the sample measuring apparatus main body S, various settings related to assay, display of assay results, and others. By communication to and from the sample measuring apparatus main body S, the processing apparatus PC can provide the sample measuring apparatus main body S with instructions and receive measurement data from the sample measuring apparatus main body S.

Additionally, the processing apparatus PC also sometimes performs processing related to the control of the sample measuring apparatus main body S. In this case, the processing apparatus PC serves as the control section of the sample measuring apparatus.

The sample measuring apparatus is an apparatus (blood assaying apparatus) that carries out assays (measurement/analysis) of blood (biological sample) accommodated within a blood collection tube 3, and primarily includes an apparatus mechanism section 2 and the casing 1 accommodating this apparatus mechanism section 2.

The casing 1 is fabricated with a synthetic resin, a steel plate subjected to rust prevention processing or the like, and is fixed to the apparatus mechanism section 2 by use of a fixing unit such as a bolt. In the right-hand bottom of one face (side face of the left side in FIG. 1) of the casing 1 is formed an opening 5, and the blood collection tube 3 can be inserted into the apparatus mechanism section 2 through this opening 5. In other words, in one edge side of the bottom of the apparatus mechanism section 2, near its edge is disposed in-and-out-freely from the above opening 5 a slider 7 having placed thereon a mounting board 6 for mounting the above blood collection tube 3. In addition, in the edge of the above slider is rotation-freely disposed a cover 8 that shuts the above opening 5; this cover 8 is annexed so as to incline outward by a predetermined angle by means of a spring, not shown (See FIG. 1). In the case where the apparatus is out of service (this state can be externally displayed by not lighting a lamp within a button 15 disposed in one face of the above casing 1), when this button 15 is pushed, the above slider 7 advances outward from the apparatus mechanism section 2. At this time, when the apparatus is out of service, the above opening 5 is shut off by means of the cover 8. If the slider 7 advances outward from the apparatus mechanism section 2, the connection between a protruded portion 8a of the cover 8 and a concave portion 9 formed in a portion of the periphery of the above opening 5 is dissolved and the cover 8 is relieved. Additionally, because the connection between the above protruded portion 8a and the concave portion 9 dissolved, the above cover 8 is inclined outward by the predetermined angle via energized force of the spring.

On the upper face of the mounting board 6 is formed a concave portion (not shown) into which the lower part of the blood collection tube 3 can be inserted. When the lower part of the blood collection tube 3 is inserted into this concave portion and the above button 15 is pushed, the above slider 7 is retracted into the apparatus mechanism section 2 and the above blood collection tube 3 is set in place. Then, the above cover 8 is raised against the energized force of the spring, the opening 5 is shut off by means of the cover 8. At this time, the above protruded portion 8a and concave portion 9 are connected, so the opening of the cover 8 is prevented. Subsequently, sure shut-off of the opening 5 via the cover 8 is detected by means of a detection unit such as a micro switch, which is set such that a subsequent sample sucking step and the like are possible.

Additionally, a part (side face of the right-hand side in FIG. 1) of the side face of the casing 1 is fixed in the apparatus mechanism section 2 via a bolt 10 in such a way that inspection, maintenance and the like of the inside of the apparatus mechanism section 2 can be readily conducted. Moreover, in FIG. 1, reference numeral 16 is mainly an air outlet for releasing heat outside generated within the apparatus mechanism section 2 by means of a fan (not shown).

The apparatus mechanism section 2 includes a sample setting section 4 for setting the above blood collection tube 3 in place within the apparatus, a sample preparation section for preparing a sample for assays such as quantifying and diluting blood in the blood collection tube 3, and measurement sections D1, D2, and D3 of performing measurement of blood diluted or the like.

[Sample Setting Section]

The sample setting section 4 is a section for setting the blood collection tube 3 having accommodated therein a sample (blood) in a sealed state in place within the apparatus mechanism section 2, and includes the mounting board 6 as discussed above, the slider 7, and a drive source (not shown) of driving this slider 7 such as a stepping motor.

[Sample Preparation Section]

The above sample preparation section is a section of preparing a sample for a variety of assays by sucking a predetermined amount of blood from the blood collection tube 3 and then mixing the blood with a reagent within a first mixing chamber (first accommodation vessel: HGB/RBC chamber) MC1, or a second mixing chamber (second accommodation vessel) MC2, and includes a sucking tube 13 of stabbing a stopper 3a that seals the blood collection tube 3 to absorb a sample within the blood collection tube 3, a horizontal drive section of horizontally transferring the sucking tube 13, a vertical drive section of vertically transferring the above sucking tube 13, and others. The horizontal drive section includes a stepping motor 28 as a drive source; the vertical drive section includes a stepping motor 68 as a drive source (see FIG. 4).

The above sucking tube 13 has therein a channel extending to the longitudinal direction, and a sucking mouth of sucking a sample or air, which can be used without particular limitation in the present invention so long as the sucking mouth is formed near the edge.

[Reagent Vessel]

As shown in fluid circuit diagrams of FIGS. 5 and 6, in the apparatus mechanism section 2 is capable of being disposed a reagent vessel for accommodating a reagent, so that the reagent vessel can be connected to the fluid circuit. Specific examples of a reagent vessel used in the embodiment include a dilution solution vessel EPK-V for accommodating a dilution solution (washing solution) EPK, a hemoglobin hemolytic agent vessel SLS-V for accommodating the hemoglobin hemolytic agent SLS, a white blood cell-classifying hemolytic agent vessel FFD-V for accommodating the white blood cell-classifying hemolytic agent FFD of dissolving red blood cells, and a white blood cell-classifying stain solution vessel FFS-V for accommodating the white blood cell-classifying stain solution FFS.

[Sample Supply Section]

As a sample supply section for supplying a sample to the first mixing chamber MC1 and/or second mixing chamber MC2 from the blood collection tube 3, provided are the above sucking tube 13 and a whole blood sucking syringe pump SP1. The sucking tube 13 absorbs a predetermined amount of a whole blood sample from the blood collection tube 3 by means of the whole blood sucking syringe pump SP1, and transfers the amount to the positions of the first mixing chamber MC1 and second mixing chamber MC2, and then the whole blood sucking syringe pump SP1 partition-supplies the predetermined amount of the whole blood sample to the respective chambers MC1 and MC2.

[Reagent Supply Section]

The dilution solution vessel EPK-V and hemoglobin hemolytic agent vessel SLS-V are connected to each other in such a manner that a reagent can be supplied to the first mixing chamber MC1. In other words, a dilution solution is capable of being supplied to the first mixing chamber MC1 from the dilution solution vessel EPK-V by means of a diaphragm pump DP 1 for dilution solution supply (for EPK), and this diaphragm pump DP 1 for EPK includes a reagent supply section for a dilution solution.

In addition, a hemolytic agent is capable of being supplied to the first mixing chamber MC1 from the hemolytic agent vessel SLS-V by means of a diaphragm pump DP3 for hemolytic agent supply (for SLS), and this diaphragm pump DP3 for SLS includes a reagent supply section for a hemolytic agent.

The hemolytic agent vessel FFD-V and stain solution vessel FFS-V are connected to each other in such a manner that a reagent can be supplied to the second mixing chamber MC2. In other words, a hemolytic agent is capable of being supplied to the second mixing chamber MC2 from the hemolytic agent vessel FFD-V by means of a diaphragm pump DP4 for hemolytic agent (for FFD), and this diaphragm pump DP4 for FFD includes a reagent supply section for a hemolytic agent (common reagent supply section) of being a common reagent.

Moreover, a stain solution is capable of being supplied to the second mixing chamber MC2 from the stain solution vessel FFS-V by means of a diaphragm pump DP5 for stain solution (for FFD), and this diaphragm pump DP5 for FFS includes a reagent supply section for a stain solution (exclusive reagent supply section).

[Reagent Feed Channel]

A reagent feed channel from the dilution solution vessel EPK-V to the first mixing chamber MC1 and a reagent feed channel from the hemolytic agent vessel SLS-V to the first mixing chamber MC1 are joined at a juncture CR1 on the way, a reagent feed channel T1 common to both reagents is connected to the first mixing chamber MC1 (see FIG. 5).

[Characteristics to be Measured]

A sample measuring apparatus of the embodiment can measure and assay a plurality of measurement target particle components like red blood cells, blood platelets, white blood cells and hemoglobin in blood. More specifically, a sample measuring apparatus of the embodiment can measure and assay many measurements and others such as a red blood cell number, MCV (mean corpuscular volume), a blood platelet number, a white blood cell number, classification of white blood cells and hemoglobin concentrations.

[Measurement Section]

The above measurement sections D1, D2, and D3 include an electric measurement section (measurement section by an impedance detection method) D1 of electrically measuring blood cells, an optical measurement section D2 of optically measuring blood cells, and a hemoglobin measurement section D3 of carrying out measurement on hemoglobin by means of a SLS hemoglobin method.

The electric measurement section D1 measures red blood cells and blood platelets as measurement target particle components. Additionally, the optical measurement section D2 primarily measures white blood cells as measurement target particle components, and can also measure red blood cells and blood platelets as measurement target components.

The above first mixing chamber MC1 is a section of preparing a sample for the purpose of assaying red blood cells, blood platelets and hemoglobin; a sample prepared in the first mixing chamber MC1 is used in measurement in the electric measurement section D1 and third measurement section D3 and, as required, also used in measurement in the second measurement section D2.

The above second mixing chamber MC2 is a section of preparing a sample for the purpose of assaying white blood cells; a sample prepared in the second mixing chamber MC2 is used in measurement in the second measurement section D2.

[Electric Measurement Section: RBC/PLT Measurement Section]

The electric measurement section D1 is configured as a RBC/PLT measurement section of determining two measurements of the numbers of red blood cells and blood platelets for the two target components of red blood cells and blood platelets. This RBC/PLT measurement section D1 can electrically measure RBC and PLT by means of the sheath flow DC detection method.

In addition, electric measurement of blood cells (impedance detection) includes an electric resistance mode (Direct Current: DC mode) and an electric capacitance mode, each being capable of being adopted as an electric measurement section. The former counts blood cells by detecting resistance changes when blood cells pass through pours; the latter counts blood cells by detecting electric capacitance changes when blood cells pass through pours.

In other words, both of them detect changes in impedance. The impedance detection mode detects a change in the above impedance as a pulse. The total number of pulses is the total number of blood cells passed through pours, and the size of a pulse is detected as the size of each blood cell.

[Optical Measurement Section: WBC/RBC/PLT Measurement Section]

The optical measurement section D2 is configured as an optical detection section of being capable of carrying out measurement on many measurements and others like white blood cell counts and white blood cell classification for the target component, white blood cell. This optical detection section D2 can perform white blood cell counting and white blood cell classification by flow cytometry using a semiconductor laser.

Additionally, the optical measurement of blood cells includes, in addition to flow cytometry, nephelometry, blood cell immobilization, and others, each being capable of being adopted as an optical measurement section D2.

Moreover, the optical measurement section D2, like the electric measurement section D1, is used also as the RBC/PLT measurement section that performs the RBC measurement (measurement of the number of red blood cells) and PLT measurement (measurement of the number of blood platelets). That is, the optical measurement section D2 is the WBC/RBC/PLC measurement section.

The configuration of the optical measurement section D2 will be set forth in detail later.

[HGB Measurement Section]

The HGB measurement section D3 is configured as an HGB measurement section of carrying out HGB measurement (measurement of the amount of hemoglobin in blood). This HGB detection section D3 can perform HGB measurement by means of the SLS-hemoglobin method.

[Control Section]

As shown in FIG. 4, the apparatus mechanism section 2 includes a control section 100 of controlling the above sample preparation section and the measurement sections D1, D2, and D3. Additionally, the apparatus mechanism section 2 also includes a drive circuit section 110 for driving magnetic valves SV1 to SV33, SV40 and SV41 and a variety of pump motors 28, 68, SP1, SP2, P, V, DP1, DP2, DP3, DP4 and DP5 and others, all constituting the sample preparation section and the like; the control section 100 drives the magnetic valves and others via the drive circuit section 110.

The control section 100 is capable of communicating the processing apparatus PC via a communication interface (not shown), and can communicates various signals, data and others with the processing apparatus PC.

[Measurement Modes According to Species of Animals]

The sample measuring apparatus main body S relates to the measurements of red blood cells and blood platelets, and has two measurement modes of the first and second measurement modes.

The first measurement mode measures a mixed sample for red blood cells and blood platelets only by means of the electric measurement section D1. The first measurement mode is used in the case where a biological sample is s blood sample capable of discrimination of red blood cells and blood platelets even by means of the electric measurement section D1, such as samples of dogs and others.

The second measurement mode measures a mixed sample for red blood cells and blood platelets by means of both of the electric measurement section D1 and optical measurement mode D2. The second measurement mode is used in the case where a biological sample is a blood sample incapable of discrimination of red blood cells and blood platelets by means of the electric measurement section D1, such as a sample of cats and others.

The above control section 100 controls the measurement sections D1, D2 and D3 so that measurement according to measurement modes in the measurement sections D1, D2 and D3 is carried out.

[Input Section of Species of Animals (Species of Samples)]

Users of the sample measuring apparatus can input a species of an animal of a biological sample through the use of the processing apparatus PC. The processing apparatus PC has a screen display function in order for a user to select species of animals (e.g., a dog, cat, horse, or others) on the screen and a function of receiving an input for selecting a species of an animal from a mouse/key board, and the like as functions for input of species of animals, and these functions constitute input sections of species of animals.

[Measurement Mode Selection Based on Animal Species]

As illustrated in FIG. 9, when a user inputs an animal species by means of an animal species input (Step S11), the processing apparatus PC selects a measurement mode corresponding to an input animal species, referring to an animal species database shown in FIG. 10. Additionally, in the animal species database, a measurement mode to be executed is registered for every animal species.

For instance, if a dog is input as a species of an animal, the first measurement mode is selected and the processing apparatus PC transmits an instruction of carrying out measurement in the first measurement mode to the sample measurement apparatus main body S (Step S13). If so, the sample measurement apparatus main body S works so as to perform measurement in the first measurement mode and transmits its measurement data to the processing apparatus PC.

When the processing apparatus PC receives measurement data in the first measurement mode from the sample measurement apparatus main body S (Step S14), the PC data-processes the measurement data (Step S15), and displays the processed results in a predetermined display format on the screen or stores them in a file.

In addition, if a cat is input, for example, as a species of an animal, in measurement mode selection (Step S12) is selected the second measurement mode (see FIG. 10), and the processing apparatus PC transmits the instruction of carrying out measurement in the second measurement mode to the sample measurement apparatus main body S (Step S16). The sample measurement apparatus main body S that has received the second measurement mode instruction signal works so as to perform measurement in the second measurement mode, and transmits its measurement data to the processing apparatus PC. When the processing apparatus PC receives measurement data in the second measurement mode from the sample measurement apparatus main body S (Step S17), the PC data-processes the measurement data (Step S18), and displays the processed results in a predetermined display format on the screen or stores them in a file.

[Measurement Section Used in Each Measurement Mode]

FIG. 11 shows a measurement section used in the first measurement mode; FIG. 12 shows a measurement section used in the second measurement mode.

The sample measurement apparatus of the embodiment can measure a plurality of measurements and others such as a red blood cell number, MCV (mean corpuscular volume), a blood platelet number, a white blood cell number, white blood cell classification and a hemoglobin concentration. Of these characteristics and others, a white blood cell number, white blood cell classification and a hemoglobin concentration are measured in a similar manner in both measurement modes.

On the other hand, the red blood cell number, MCV (mean corpuscular volume) and blood platelet number are different in measurement section or calculation method in both measurement modes.

Hereinafter, first, the measurement of white blood cell (counting and classification) carried out simultaneously separately from the measurements of red blood cells and blood platelets will be set forth, and subsequently the measurements of red blood cells and blood platelets as well as hemoglobin will be described.

[WBC Measurement]

The sample measuring apparatus main body S mixes a whole blood sample (11 μL) with a hemolytic agent (1 mL) to prepare a measurement sample for white blood cells for the measurement regarding the white blood cell, and measures the number of white blood cells and five classes of white blood cells, for this measurement sample, in the optical measurement section D2 of being the second measurement section by flow cytometry.

FIG. 13 indicates the work procedure of the sample measuring apparatus main body S for white blood cell measurement. The work procedure will be set forth also with reference to the fluid circuit diagrams of FIGS. 5 to 8 hereinafter. First, a hemolytic agent FFD (0.5 mL) is supplied to the second mixing chamber MC2 from the hemolytic agent vessel FFD-V (Step S21).

Specifically, Step S21 involves opening a valve SV19 and closing a valve SV20 as well as opening a valve SV22 and closing a valve S21 and negative-pressure driving a diaphragm pump D4 for FFD, thereby supplying 0.5 mL of the hemolytic agent FFD to the diaphragm pump D4 for FFD from the hemolytic agent vessel FFD-V.

Thereafter, Step S21 involves closing the valve SV19 and opening the valve SV20 as well as opening the valve S21 and closing the valve SV22 and negative-pressure driving a diaphragm pump D4 for FFD, thereby supplying 0.5 mL of the hemolytic agent FFD to the second mixing chamber MC2 by means of the diaphragm pump D4.

Furthermore, Step S21 involves opening the valve SV19 and closing the valve SV20 as well as closing a valve S21 and opening a valve SV22 and negative-pressure driving the FFD diaphragm pump D4, and again supplying 0.5 mL of the hemolytic agent FFD to the diaphragm pump D4 for FFD from the hemolytic agent vessel FFD-V.

Next, the whole blood sample of the blood collection tube 3 is quantitatively absorbed by means of the sucking tube 13 (piercer) (Step S22). Specifically, Step 22 involves inserting the sucking tube 13 into the blood collection tube 3, and driving the whole blood sucking syringe pump SP1 to quantitatively absorb the whole blood sample (20 μL).

Subsequently, the sucking tube 13 is withdrawn from the blood collection tube 3 and brought down to the second mixing chamber MC2 (Step S33). In this state, the whole blood sucking syringe pump is driven to eject 11 μL of the whole blood sample (portion of the sample absorbed in Step S22) to the second mixing chamber MC2 from the sucking hole of the sucking tube 13 (Step S24).

After completion of the ejection, the stain solution (exclusive reagent) FFS is placed into the second mixing chamber MC2 (Step S25). Specifically, Step S25 involves, with the valve SV40 for stain solution replenishment being opened and the valve SV41 for stain solution supply being closed, opening the valve SV22 and closing the valve SV21 and negative-pressure driving the diaphragm pump (diaphragm pump for FFS) DP5 for stain solution supply, thereby replenishing 20 μL of the stain solution FFS to the diaphragm pump DP5 for FFS. Further, Step S25 involves closing the valve SV40 and opening the valve SV41 as well as opening the valve SV21 and closing the valve SV22 and positive-pressure driving the diaphragm pump DP5 for FFS to place 20 μL of the stain solution FFS into the second mixing chamber MC2. Additionally, as exclusive reagents, other reagents, for example, a dilution solution and a buffer solution may be contained, and only a dilution solution or buffer solution may be an exclusive reagent. Subsequently, the hemolytic agent (common reagent) FFD is placed into the second mixing chamber MC2 (Step S26). Namely, the valve SV22 and valve SV19 are closed, and the valve SV21 and SV20 are opened, and then 0.5 mL of the hemolytic agent FFD is placed into the second mixing chamber MC2 by means of the diaphragm pump DP4 for FFD. The whole blood sample is poured thereinto and agitated to dissolve the red blood cells in the second mixing chamber MC and produce a white blood cell measurement sample in which the white blood cells are stained (Step S27).

Then, the white blood cell sample of the second mixing chamber MC2 is transported to the optical measurement section (WBC/RBC/PLT measurement section) D2, and the measurement of the white blood cells is carried out in the optical measurement section D2 (Step S28). Specifically, Step S28 involves opening the valves SV4, SV29, and SV22, and closing the valve SV21 to drive the diaphragm pump DP2 for charging and precisely charge 1.0 mL of the white blood cell measurement sample. Thereafter, Step S28 involves closing the valves SV4, SV29 and SV22 to complete the charging to the optical measurement section D2.

Subsequently, the valves SV9 and SV31 are opened to supply the sheath solution (dilution solution) EPK to the optical measurement section D2 from the EPK accommodation vessel EPK-C. Then, the valve SV3 is opened and the sample supplying syringe pump SP2 is driven, with the valve SV1 being closed, and measurement is carried out in the optical measurement section D2.

[Optical Measurement Section (WBC/RBC/PLT Measurement Section)]

FIG. 14 shows a schematic configuration of the optical measurement section D2 of being the second measurement section. This optical measurement section D2 transports a measurement sample to a flow cell 101, generates a liquid flow in the flow cell 101, and irradiates the blood cells contained in liquid flow that passes through the flow cell 101 with semiconductor laser light for measurement, and has a sheath flow system 100, beam spot forming system 110, forward scattered light receiving system 120, side scattered light receiving system 130 and side fluorescence receiving system 140.

The sheath flow system 100 flows a sample enclosed by the sheath solution and arranged in line in the flow cell 101, thereby improving the precision and reproducibility of the blood cell count. The beam spot forming system 110 is configured in such a way that the light radiated from a semiconductor laser 111 passes through a collimator lens 112 and a condenser lens 113 and is directed onto the flow cell 101. Additionally, the beam spot system 110 also includes a beam stopper 114.

The forward scattered light receiving system 120 is configured to collect scattered light to the forward direction by means of a forward collection lens 121 and receive the light passed through a pin hole 122 by means of a photodiode (forward scattered light receiving system) 123.

A side scattered light receiving system 130 is configured to collect scattered light to the side direction by means of a side light collecting lens 131 as well as reflect a portion of the light via a dichroic mirror 132 and receive the portion of the light by means of a photodiode (side scattered light receiving section) 133.

Light scattering is a phenomenon that is generated when particles like blood cells are present in the direction of light and the light is changed in its direction. The detection of this scattered light enables the obtainment of information on the size and material of particles. In particular, information on the size of particles (blood cells) can be obtained from the forward scattered light. In addition, information inside a particle can be obtained from the side scattered light. When blood cell particles are irradiated with laser light, the intensity of the side scattered light depends on the complexity of the inside of a cell (shape, size and density of the nucleus, and particle amount). Accordingly, the utilization of the properties of the side scattered light intensity enables the measurement of the number of blood cells, upon classification (discrimination) of blood cells.

The side fluorescence receiving system 140 is configured so as to further pass the light reflected via the dichroic miller 132 through a spectral filter 141 and receive a photomultiplier (fluorescence receiving section) 142.

When a fluorescent material like a stained blood cell is irradiated with light, the light of wavelength that is longer than that of irradiated light is emitted. The intensity of fluorescent light is high when blood cells are well stained; the measurement of this fluorescence intensity is capable of obtaining information on the stain degree of blood cells. Thus, the difference of the (side) fluorescent light intensity enables the determination of classification of white blood cells and others.

When light is received by each of the light receiving sections 123, 133 and 142, the each of the light receiving sections 123, 133 and 142 outputs electric pulse signals. From these electric pulse signals are produced measurement data. The measurement data are transmitted from the sample measuring apparatus main body S to the processing apparatus PC (Step S14, Step 17), and processed and analyzed in the processing apparatus PC.

When the processing apparatus PC receives the measurement data of white blood cells from the optical measurement section D2, the PC counts the number of the white blood cells and classifies the white blood cells (classification in terms of five categories of lymph cells, neutrophilic leukocytes, eosinophilic leukocytes, basophilic leukocytes and monocytes) in the white measurement sample on the basis of the scattered received light in the scattered light receiving section and the received fluorescent light in the fluorescence receiving section (side received fluorescent light).

FIG. 15 is a scattergram of white blood cell classification displayed in the processing apparatus PC. In this scattergram, the X-axis represents the side scattered light intensity and the Y-axis represents the fluorescence intensity; the white blood cells are classified into five sets of lymph cells, neutrophilic leukocytes, eosinophilic leukocytes, basophilic leukocytes and monocytes. As can be seen from this scattergram, the processing apparatus PC divides the white blood cells into five blood cell groups and detects them. The processing apparatus PC further carries out a variety of processes, including calculations of the number of blood cells in each class, the ratios of the numbers among classes, and others.

[RBC/PLT/HGB Measurements]

In both of the first and second measurement modes, of the whole blood samples absorbed in the sucking tube 13, the residual whole blood samples not used for assays on white blood cells are used as samples for measurement of red blood cells, blood platelets and hemoglobin in the first mixing chamber MC1, and the samples are measured in the electric measurement section D1 and HGB measurement section D3 and are also measured further in the optical measurement section D2 in the case of the second measurement mode.

[RBC/PLT/HGB Measurements in the First Measurement Mode]

When the RBC/PLT measurements and HGB measurement are conducted, a mixture sample for the RBC/PLT measurements and a mixture sample for the HGB measurement are required. A reagent for preparing the mixture sample for the RBC/PLT measurements is different from a reagent for preparing the mixture sample for the HGB measurement, so they need to be separately prepared; for the preparation of these mixture samples, two mixing chambers are usually needed.

On the contrary, in the embodiment, two mixture samples are prepared by means of one mixing chamber (first mixing chamber: HGB/RBC/PLT chamber) MC1. A measurement procedure including this preparation procedure will be set forth in detail on the basis of FIGS. 16 and 17 also with reference to the fluid circuit diagrams of FIGS. 5 to 8 hereinafter.

[Preparation and Measurement of an RBC/PLT Measurement Sample in the First Measurement Mode]

First, Step S22 (see FIG. 13) involves quantitatively sucking the whole blood sample (20 μL) of the blood collection tube (piercer) 3, specifically, inserting the sucking tube 13 into the blood collection tube 3, and driving the whole blood sucking syringe pump SP1 to quantitatively suck the whole blood sample.

Thereafter, about 1 mL of the dilution solution EPK of being the first reagent is supplied to the first mixing chamber MC1 (Step S31). Specifically, Step S31 involves opening the valve SV23 for about 1.0 sec in order to discharge the liquid within the first mixing chamber MC1, opening the valves SV21 and SV24, and supplying 1.0 mL of the dilution solution EPK to the first mixing chamber MC1 by use of the diaphragm pump D1 for a dilution solution (for EPK) having replenished therein the dilution solution EPK in advance, and subsequently closing the valves SV21 and Sv24 and opening the valves SV22 and SV32 to replenish the dilution solution EPK to the diaphragm pump DP 1 for EPK.

Next, the sucking tube 13 is brought down to the first mixing chamber MC1 (Step S32), and 4 μL of the whole blood sample is ejected to the first mixing chamber MC1 from the sucking hole of the sucking tube 13 (Step S33). Additionally, Steps S32 and S33 are executed immediately after Step S24 (see FIG. 13) is executed.

Upon completion of the ejection, about 1 mL of the dilution solution EPK of being the first reagent is supplied again to the first mixing chamber MC1 (Step S34). Specifically, Step S34 involves closing the valves SV22 and SV32, and opening the valves SV21 and SV24 after completion of the ejection in order to again supply 1.0 mL of the dilution solution EPK to the first mixing chamber MC1 by means of the diaphragm pump DP1 for EPK. This agitates the whole blood sample (4 μL) and the dilution solution EPK (2 mL) within the first mixing chamber MC1 to prepare red blood cell and blood platelet measurement sample (RBC/PLT measurement sample) (Step S35).

After preparation of the RBC/PLT measurement sample, the valves SV21 and SV24 are closed and the valves SV22 and SV32 are opened for the replenishment of the dilution solution EPK to the diaphragm pump for EPK.

Then, a portion (1.0 mL) of the RBC/PLT measurement sample is supplied to the RBC/PLT measurement section (electric section: first measurement section) (Step S36). Specifically, Step S36 involves opening the valves SV2 and SV25 to charge precisely 1.0 mL (portion of the RBC/PLT measurement sample within the first mixing chamber MC1) of the RBC/PLT measurement sample to the fluid channel between the first mixing chamber MC1 and electric measurement section D1 by means of the diaphragm pump DP2 for charging, closing the valves SV2, SV25, SV22 and SV32 to complete charging, and further opening the valves SV8 and SV9 to supply a sheath solution for measurement to the electric measurement section D1. The RBC/PLT measurement sample thus charged is supplied to the electric measurement section D1, and then the measurement of the numbers of red blood cells and blood platelets is performed by means of the DC system (Step S37).

When the animal species is a dog, the measurement results of the numbers of red blood cells and blood platelets by means of the electric measurement section D1 are like a histogram indicated in FIG. 24. In other words, the number of blood cells is measured for every size of blood cells. In addition, the left side of the threshold a1 corresponds to the number of blood platelets and the right-hand side of the threshold corresponds to the number of red blood cells; an appropriate setting of the threshold a1 enables the discrimination of the blood platelet and red blood cell.

Additionally, since the precise size of each blood cell can be obtained in the electric measurement section D1, the MCV (mean corpuscular volume) can be calculated from the number of red blood cells and the size of each red blood cell of being measurement results in the electric measurement section D1. This calculation is performed in the processing apparatus PC.

In this manner, in the first measurement mode, measurement results on each measurement of the number of blood platelets, the number of red blood cells and the MCV on the basis of the measurement results of the electric measurement section D1.

[Preparation and Measurement of an HGB Measurement Sample in the First Measurement Mode]

Even though the RBC/PLT measurements are completed, 1 mL of a sample is present as a residual sample in the first mixing chamber MC1. For the preparation of the HGB measurement sample, the hemolytic agent SLS is further supplied to the first mixing chamber MC1 where the residual sample is present (Step 38). Specifically, Step S38 involves opening the valves SV21 and SV18, and supplying the hemolytic agent SLS to the first mixing chamber MC1 by means of the diaphragm pump DP3 for a hemoglobin hemolytic agent (for SLS) having replenished thereto the hemolytic agent SLS in advance. This agitates the hemolytic agent SLS and the above residual sample to prepare the HGB measurement sample prepared by mixing the hemolytic agent SLS (0.5 mL) with the above residual sample (1.0 mL) (Step S38).

Thereafter, the mixing sample for HGB measurement is allowed to react (Step S39). While this sample is allowed to react, at an arbitrary time, the valves SV21 and SV27 are opened to discharge the diaphragm pump DP2 for charging for the preparation of the next charging. Subsequently, the valves SV22 and SV28 are opened to initiate the charging of the mixing sample for the HGB measurement to the HGB detection section D2, and the valves SV22 and SV28 are closed to complete the charging (Step 40). Then, the HGB measurement is carried out (Step S41).

[Measurements of RBC/PLT/HGB in the Second Measurement Mode]

Next, a measurement procedure including a preparation procedure of a sample in the second measurement mode will be set forth in detail on the basis of FIGS. 18 and 19 also with reference to the fluid circuit diagrams of FIGS. 5 to 8.

[Preparation of the RBC/PLT Measurement Sample in the Second Measurement Mode]

First, Step S22 (see FIG. 13) involves quantitatively sucking the whole blood sample (20 μL) of the blood collection tube 3 by means of the sucking tube (piercer) 13. Specifically, Step S22 involves inserting the sucking tube 13 into the blood collection tube 3 and driving the whole blood sucking syringe pump SP1 to quantitatively suck the whole blood sample.

Thereafter, about 2.0 mL of the dilution solution EPK of being the first reagent is supplied to the first mixing chamber MC1 (Step S51). Specifically, Step S51 involves opening the valve SV23 for about 1.0 sec to discharge the liquid within the first mixing chamber MC1, opening the valves SV21 and SV24 to supply 2.0 mL of the dilution solution EPK to the first mixing chamber MC1 by means of the diaphragm pump D1 for a dilution solution (for EPK) having replenished thereto the dilution solution EPK in advance, closing the valves SV21 and SV24 and opening the valves SV22 and SV32 to replenish the dilution solution EPK to the diaphragm pump DP1 for EPK, closing the valves SV22 and SV32 and opening the valves SV21 and SV24 in order to again supply 1.0 mL of the dilution solution EPK to the first mixing chamber MC1 by means of the diaphragm pump DP1 for EPK, and subsequently closing the valves SV21 and SV24 and opening the valves SV22 and SV32 to replenish the dilution solution EPK to the diaphragm pump DP1 for EPK.

Next, the sucking tube 13 is brought down to the first mixing chamber MC1 (Step S52), and 6 μL of the whole blood sample is ejected to the first mixing chamber MC1 from the sucking hole of the sucking tube 13 (Step S53). Additionally, Steps S52 and S53 are executed immediately after Step s24 (see FIG. 13) is executed.

After completion of the ejection, about 1.0 mL of the dilution solution EPK of being the first reagent is supplied again to the first mixing chamber MC1 (Step S54). Specifically, Step S54 involves closing the valves SV22 and SV32 and opening the valves SV21 and SV24 after completion of the ejection in order to supply 1.0 mL of the dilution solution EPK to the first mixing chamber MC1 by means of the diaphragm pump DP1 for EPK. This agitates the whole blood sample (6 μL) and dilution solution EPK (3.0 mL) within the first mixing chamber MC1 to prepare red blood cell and blood platelet measurement sample (RBC/PLT measurement sample) (Step S55).

Additionally, after the RBC/PLT measurement sample is prepared, for the replenishment of the dilution solution EPK to the diaphragm pump for EPK, the valves SV21 and SV24 are closed and the valves SV22 and SV32 are opened.

The second measurement mode is larger in the amounts of the whole blood sample and the dilution solution used in the RBC/PLT measurements than the first mode. This is because the second measurement mode uses not only the first measurement section D1, but the second measurement section D2 for the measurements of red blood cells and blood platelets, so a larger amount of measurement sample is needed.

For the above processing, the control section 100 carries out the control in such a manner that a large; amount of the whole blood sample and/or the reagent (dilution solution) is supplied to the first mixing chamber MC1 in the second measurement mode than in the first measurement mode. In other words, the control section 100 has a function of changing the amount of a biological sample depending on the species of animals (sample species). Additionally, the control section 100 has a function of changing the amount of a reagent depending on the species of animals (sample species).

Further, the control section 100 may also has a function of changing the kind of a reagent mixed in a sample depending on the species of animals (measurement mode).

[Measurement in the Electric Measurement Section by Means of the Second Measurement Mode]

Subsequently, a portion (1.0 mL) of the RBC/PLT measurement sample is supplied to the RBC/PLT measurement section (electric measurement section: first measurement section) (Step S56). Specifically, Step S56 involves opening the valves SV2 and SV25 to charge precisely 1.0 mL (portion of the RBC/PLT measurement sample within the first mixing chamber MC1) of the RBC/PLT measurement sample to the fluid channel between the first mixing chamber MC1 and electric measurement section D1 by means of the diaphragm pump DP2 for charging, closing the valves SV2, SV25, SV22 and SV32 to complete charging, and further opening the valves SV8 and SV9 to supply a sheath solution for measurement to the electric measurement section D1. The RBC/PLT measurement sample thus charged is supplied to the electric measurement section D1, and then the measurement of the numbers of red blood cells and blood platelets in the sample is performed by means of the DC system (Step S57). In the second measurement mode, the measurements of the numbers of red blood cells and blood platelets are performed in the second measurement section as discussed below; the measurement results in the first measurement section D1 are primarily used for the calculation of the MCV (mean corpuscular volume).

When the animal species is a cat, the measurement results of the numbers of red blood cells and blood platelets by means of the electric measurement section D1 are like a histogram indicated in FIG. 25. In other words, the number of blood cells is measured for every size of blood cells. However, when the animal species is a cat, since blood platelets the size of witch is substantially the same as the size of red blood cells are present in the blood, the electric measurement section D1 can count the number of blood cells for every size of blood cells, but cannot discriminate blood platelets and red blood cells. Namely, in the left side of the threshold a2, not only blood platelets but also red blood cells are contained; in the right-hand side of the threshold a2, not only blood platelets but also red blood cells are contained.

However, the measurement results of the electric measurement section D1, indicating a precise size of blood cells, are used for calculating the MCV along with the measurement results of the optical measurement section (second measurement section) D2 (details are described later).

[Measurement in the Optical Measurement Section by Means of the Second Measurement Mode]

Another portion (1.0 mL) of the RBC/PCT measurement sample within the first mixing chamber MC1 is supplied to the optical measurement section (second measurement section) D2 (Step S58). Specifically, Step S58 involves opening the valves SV2, SV1, SV3, SV29 and SV22 and closing the valve SV21 to thereby drive the diaphragm pump DP2 for charging and charge precisely 1.0 mL of the other portion of the RBC/PCT measurement sample, and then closing the valves SV2, SV1, SV3, SV29 and SV22 to complete the charging to the optical measurement section D2.

Thereafter, the valves SV9 and SV31 are opened to thereby supply the sheath solution (dilution solution) EPK to the optical measurement section D2 from the EPK accommodation vessel EPK-C. Then, the valve SV3 is opened and the sample supplying syringe pump SP2 is driven, with the valve SV1 being closed, and the measurement is carried out in the optical measurement section D2 (Step S59). In the optical measurement section D2, the measurements of red blood cells and blood platelets are performed by flow cytometry.

The measurement data output from each of the light receiving sections 123, 133 and 142 of the optical measurement section D2 are transmitted from the sample measuring apparatus main body S to the processing apparatus PC, and in the processing apparatus PC the processing and assay are carried out.

The processing apparatus PC, when receiving the measurement data of the red blood cells and blood platelets from the optical measurement section D2, performs the discrimination between the red blood cells and blood platelets contained in the RBC/PLT measurement sample and the calculation of the numbers of red blood cells and blood platelets on the basis of the forward scattered light in the forward scattered light receiving section 123 and side scattered light in the side scattered light receiving section 133.

FIG. 20 is a scattergram of the red blood cells and blood platelets displayed on the processing apparatus PC. In this scattergram, the X-axis represents the side scattered light intensity and the Y-axis represents the forward scattered light intensity; a set of the red blood cells and a set of blood platelets are separated (blood cell inner information between the red blood cells and blood platelets is different, so they can be discriminated even if the size of blood cells is the same). On the basis of this scattergram, the processing apparatus PC discriminates between the red blood cells and a set of blood platelets and further carries out a variety of processes such as the calculations of the numbers of red blood cells and blood platelets, the ratio between the number of red blood cells and the number of blood platelets, and others.

Additionally, the numbers of red blood cells and blood platelets need not be calculated only from the measurement results of the optical measurement section D2; the numbers of red blood cells and blood platelets may be calculated on the basis of the ratio between the number of red blood cells and the number of blood platelets obtained from the measurement results of the optical measurement section D2 and by distributing the total number of blood cells of being the measurement results of the electric measurement section D1 to each of the blood cells.

The optical measurement section D2 can discriminate between red blood cells and blood platelets, but can not provide a precise size of each of the blood cells. That is, in the optical measurement section D2, the number of blood cells per intensity of (forward) scattered light can be obtained, but it is not clear if the scattered light intensity indicates what the exact size is.

Thus, the processing apparatus PC uses the measurement results of the electric measurement section D1 indicating precise sizes of blood cells and the number of blood cells at their sizes and the measurement results of the optical measurement section D2 from which the number of each of the red blood cells and blood platelets is obtained, for the calculation of the MCV.

In other words, the number of red blood cells for every size substantially forms a normal distribution, so the processing apparatus PC can render the sizes of blood cells in the measurement results of the electric measurement section D1 to correspond to the sizes of blood cells in the measurement results of the optical measurement section D2, from the distributions of the numbers of blood cells of the two measurements sections D1 and D2. From this correspondence, the numbers of red blood cells for the precise sizes of respective blood cells are obtained, whereby the MCV is calculated.

[Preparation and Measurement of the HGB Measurement Sample in the Second Measurement Mode]

The description of the preparation and measurement of the HGB sample will be omitted since it is as in the first measurement mode.

In the embodiment, the system in the second measurement mode is configured so as to supply the RBC/PLT sample to both of the electric measurement section and optical measurement section, but the system may be configured so as to supply the RBC/PLT sample to only the optical measurement section.

[Modified Example 1 of the Measurement Sections D1, D2 and D3]

FIGS. 21 and 22 show Modified Examples of the measurement sections D1, D2 and D3. An optical measurement section D2 related to the modified example is configured as an electric and optical composite measurement unit. Additionally, unless otherwise specified herein, a sample measuring apparatus related to the modified example is the same as described in FIGS. 1 to 20.

This electric and optical composite measurement unit D2 is the one disclosed in Japanese Patent Laid-Open No. 7-128217. In other words, this composite measurement unit D2 integrally includes the functions of both of the electric measurement section D1 and optical measurement section D2 indicated in FIG. 4, and can perform measurements based on different measurement principles by means of a single measurement unit. Outputs of the composite measurement unit D2 of FIGS. 21 and 22 include an electric measurement output based on an electric measurement function and an optical measurement output based on an optical measurement function.

If the first measurement mode is selected, red blood cells and blood platelets are measured only in the electric measurement section D1 as indicated in FIG. 21. In the composite measurement unit D2, only the measurement of white blood cells is carried out. Namely, both of the outputs of the composite measurement unit D2 are used for the counting and classification of the white blood cells.

On the other hand, if tile second measurement mode is selected, as shown in FIG. 22, red blood cells and blood platelets are measured not only in the electric measurement section D1, but also in the composite measurement unit D2. That is, the optical measurement output by means of the optical measurement function of the composite measurement unit is used in counting of the numbers of red blood cells and blood platelets.

Then, the MCV is calculated in the processing apparatus PC, on the basis of the measurement results of the electric measurement section D1 and the optical measurement output of the composite measurement unit.

Additionally, in the second measurement mode as well, both of the outputs of the composite measurement unit D2 are used for the counting and classification of white blood cells.

[Modified Example 2 of the Measurement Sections D1, D2 and D3]

FIG. 23 indicates the modified example of the measurement sections D1, D2 and D3. The electric measurement section D1 related to the modified example is configured as an electric and optical composite measurement unit. Additionally, unless otherwise specified herein, a sample measuring apparatus related to the modified example is the same as described in FIGS. 1 to 20.

This electric and optical composite measurement unit D1 is also the one disclosed in Japanese Patent Laid-Open No. 7-128217. In other words, this composite measurement unit D1 integrally includes the functions of both of the electric measurement section D1 and optical measurement section D2 indicated in FIG. 4, and can perform measurements based on different measurement principles by means of a single measurement unit. Outputs of the composite measurement unit D1 of FIG. 23 include an electric measurement output based on an electric measurement function and an optical measurement output based on an optical measurement function.

If the first measurement mode is selected, the numbers of red blood cells and blood platelets are measured by the electric measurement function of the composite measurement unit D1, and the optical measurement function is not used.

On the other hand, if the second measurement mode is selected, the numbers of red blood cells and blood platelets are measured by the optical measurement function of the composite measurement unit D1. Additionally, in the second measurement mode, if the MCV needs to be also calculated, not only the optical measurement function of the composite measurement unit D1 but also the electric measurement function may also be used.

If, like the composite measurement unit D1 related to Modified Example 2, a single measurement unit D1 is measured based on a plurality of measurement principles, the control of the measurement is made easy since the unit can correspond to both measurement modes without changing the supply target of a sample.

The present invention is by no means limited the above embodiments. For instance, the measurement principles of each of the measurement sections are not limited to an electric mode and optical mode, and can adopt a wide variety of measurement principles. Additionally, the kind of samples of being the standard of measurement section selection is not limited to animal species, and for example sample species in the case where the adult and infant of humans are discriminated may be adopted.

Furthermore, the kind of samples is not limited to blood, and alternation as appropriate according to a target wanted to be measured is possible.

Moreover, in the above embodiments, the sample measuring apparatus is constructed of the sample measuring apparatus main body S and the processing apparatus PC separated therefrom, but a single apparatus may include both functions of the sample measuring apparatus main body S and processing apparatus PC.

What is claimed is:

1. A sample measuring apparatus of measuring a component in a blood sample, comprising:
   an input section adapted to input species of animal;
   a preparation section adapted to prepare a measurement sample for counting red blood cells and platelets by mixing the blood sample with a reagent;
   an electric measurement section adapted to electrically measure blood cells, wherein the electric measurement section generates for each blood cell an impedance signal that reflects a size of the blood cell;
   an optical measurement section adapted to optically measure the blood cells, wherein the optical measurement section comprising a light source that irradiates blood cells and a light detector that detects a scattered light intensity from the irradiated blood cell and generates an optical signal according to the scattered light intensity;
   a controller comprising a central processing unit (CPU) and a memory,
   wherein the controller is programmed to perform instructions of carrying out steps of measuring the red blood cells and the blood platelets from the measurement sample, the steps comprising:

according to an input of animal species, setting one of a first measurement mode and a second measurement mode;

upon the first measurement mode,
- controlling the electric measurement section to obtain impedance finals from blood cells in the measurement sample prepared by the preparation section;
- discriminating the blood cells in the measurement sample into red blood cells and blood platelets based on the impedance signals; and
- counting the red blood cells and the blood platelets;

upon the second measurement mode:
- controlling the optical measurement section to obtain optical finals from the measurement sample prepared by the preparing section;
- discriminating the blood cells in the measurement sample into the red blood cells and the blood platelets based on the optical signals; and
- counting the red blood cells and the blood platelets.

2. The sample measuring apparatus of claim 1, wherein the reagent comprises a dilution solution.

3. The sample measuring apparatus of claim 1, wherein upon the first measurement mode, the controller is further programmed to perform an instruction of carrying out the step of obtaining mean volume of the discriminated red blood cells.

4. The sample measuring apparatus of claim 1, wherein the optical measurement section comprises a first detector that detects a first type of scattered light and a second detector that detects a second type of scattered light emitted from the blood cells, and
wherein upon the second measurement mode, the controller is further programmed to perform an instruction carrying out the step of discriminating the blood cells in the measurement sample into red blood cells and blood platelets based on the first type of scattered light intensity and the second type of scattered light intensity.

5. The sample measuring apparatus of claim 1, further comprising a sucking tube for sucking blood sample from a blood collection tube and supplying the sucked blood sample to the measurement sample preparation section, and
wherein upon the first measurement mode, the controller is programmed to perform an instruction carrying out the step of controlling the sucking tube to suck a first volume of blood sample, and
upon the second measurement mode, the controller is further programmed to perform an instruction carrying out the step of controlling the sucking tube to suck a second volume of blood sample, the second volume being larger than the first volume.

6. The sample measuring apparatus of claim 1, wherein
upon the first measurement mode, red blood cells and blood platelets are discriminated by a threshold value for a size of a blood cell, and
the controller is programmed to perform an instruction carrying out a step of counting blood cells having a larger size than the threshold value as the red blood cells and other blood cells having a smaller size than the threshold value as the blood platelets.

7. The sample measuring apparatus of claim 1, further comprising a supply section for supplying a measurement sample to at least one of the electric measurement section and the optical measurement section,
wherein upon the second measurement mode, the controller is further programmed to perform an instruction of carrying out the steps of:
controlling the measurement sample supply section to supply a part of the measurement sample to the electric measurement section and another part of the measurement sample to the optical measurement section;
controlling the electric measurement section to obtain the impedance signals from the blood cells in the measurement sample; and
obtaining mean volume of the red blood cells in the measurement sample based on the distribution of the number of blood cells with respect to the impedance level and a counted number of red blood cells.

* * * * *

UNITED STATES PATENT AND TRADEMARK OFFICE
CERTIFICATE OF CORRECTION

| | | |
|---|---|---|
| PATENT NO. | : 8,147,754 B2 | |
| APPLICATION NO. | : 11/729295 | |
| DATED | : April 3, 2012 | |
| INVENTOR(S) | : Takaaki Nagai et al. | |

It is certified that error appears in the above-identified patent and that said Letters Patent is hereby corrected as shown below:

Column 19, claim 1, line 6, before "from blood cells" replace "finals" with --signals--.

Column 19, claim 1, line 14, before "from the measurement" replace "finals" with --signals--.

Signed and Sealed this
Thirty-first Day of July, 2012

David J. Kappos
*Director of the United States Patent and Trademark Office*